United States Patent [19]
von Windheim et al.

[11] Patent Number: 5,362,975
[45] Date of Patent: * Nov. 8, 1994

[54] DIAMOND-BASED CHEMICAL SENSORS

[75] Inventors: Jesko von Windheim, Raleigh, N.C.; Vasudev Venkatesan, Phoenix, Ariz.

[73] Assignee: Kobe Steel USA, Research Triangle Park, N.C.

[*] Notice: The portion of the term of this patent subsequent to Feb. 8, 2011 has been disclaimed.

[21] Appl. No.: 89,170

[22] Filed: Jul. 8, 1993

Related U.S. Application Data

[63] Continuation-in-part of Ser. No. 939,446, Sep. 2, 1992, Pat. No. 5,285,034.

[51] Int. Cl.$^5$ ............................................. H01L 29/66
[52] U.S. Cl. ......................................... 257/76; 257/77; 257/414; 204/410; 204/411; 204/412; 204/424; 422/90
[58] Field of Search ............................ 257/414, 76, 77; 204/410, 411, 412, 416, 419, 431, 422, 424, 425, 426, 421; 422/90

[56] References Cited

U.S. PATENT DOCUMENTS

| | | | |
|---|---|---|---|
| 4,982,243 | 1/1991 | Nakahata et al. | 357/15 |
| 5,002,899 | 3/1991 | Geis et al. | 437/173 |
| 5,086,014 | 2/1992 | Miyata et al. | 437/103 |
| 5,132,749 | 7/1992 | Nishibayashi et al. | 357/15 |
| 5,144,380 | 9/1992 | Kimoto et al. | 357/22 |
| 5,173,761 | 12/1992 | Dreifus et al. | 357/22 |
| 5,252,294 | 10/1993 | Kroy et al. | 422/102 |

FOREIGN PATENT DOCUMENTS 0457508 11/1991 European Pat. Off. .
0518532 12/1992 European Pat. Off. .

OTHER PUBLICATIONS

*A Thermally Activated Solid State Reaction Process for Fabricating Ohmic Contacts to Semiconducting Diamond*, Moazed et al., J. Appl. Phys., vol. 68, No. 5, pp. 2246–2254, Sep. 1, 1990.
*Metal–Intrinsic Semiconductor–Semiconductor Structures Using Polycrystalline Diamond Films*, Miyata et al., Appl. Phys. Lett., vol. 60, No. 4, pp. 480–482, Jun. 27, 1992.
*Effect of Thin Interfacial SiO$_2$ Films on Metal Contacts to B-doped Diamond Films*, Fountain et al., J. Electrochem. Soc., vol. 139, No. 5, pp. 1445–1449, May, 1992.
*Use of Electroreflectance Technique in Pt/GaAs Schottky Barrier Sensor Characterization*, Lechuga et al., Sensors and Actuators, vol. 32, pp. 354–356, 1992.
*The C–V Characteristics of Schottky Barriers on Laboratory Grown Semiconducting Diamonds*, G. H. Glover, Solid State Electronics, vol. 16, pp. 973–983, 1973.
*Electrical Characteristics of Schottky Diodes Fabricated Using Plasma Assisted Chemical Vapor Deposited Diamond Films*, Gildenblat et al., Appl. Phys. Lett. vol. 53, No. 7, pp. 586–588, Aug. 15, 1988.
*Capacitance–Voltage Measurements on Metal–SiO$_2$ Diamond Structures Fabricated with (100)– and (111)–Oriented Substrates*, Geis et al., IEEE Transac- (List continued on next page.)

*Primary Examiner*—William Mintel
*Attorney, Agent, or Firm*—Bell, Seltzer, Park & Gibson

[57] ABSTRACT

A chemical sensor includes a diode or a transistor fabricated in diamond. A diamond-based diode chemical sensor includes a first diamond layer of first conductivity type and a second diamond or non-diamond layer of second conductivity type. A relatively highly doped region is formed in the first diamond layer, adjacent an electrical contact to reduce the frequency dependance of the sensor's capacitance/voltage characteristic. A diamond-based transistor sensor includes a controlling electrode such as a gate which is configured to allow a chemical external to the transistor to alter the characteristics of the transistor. Relatively highly doped regions are formed adjacent the transistor's controlling electrodes, such as the source and drain. A heater is thermally coupled to the sensor for heating the sensor to a predetermined operating temperature. A temperature monitor is also coupled to the sensor for monitoring the sensor temperature.

33 Claims, 14 Drawing Sheets

OTHER PUBLICATIONS tions on Electron Devices, vol. 38, No. 3, pp. 619–626, Mar. 1991.

*Materials Selection for Semiconductor Gas Sensors,* P. T. Moseley, Sensors and Actuators, B.6, pp. 149–156, 1992.

*Ceramic Sensor Device Materials,* T. Nenov et al., Sensors and Actuators, B.8, pp. 117–122, 1992.

*An Application of Carbon–Type Semiconductors for the Construction of a Humidity–Sensitive Diode,* J. P. Lukaszewicz, Sensors and Actuators, B.6, pp. 61–65, 1992.

*Hydrogenated Amorphous Silicon Technology for Chemically Sensitive Thin–Film Transistors,* L. Mariucci et al., Sensors and Actuators, B.6, pp. 29–33, 1992.

*Ammonia Sensitivity of Pt/GaAs Schottky Barrier Diodes. Improvement of the Sensor with an Organic Layer,* L. M. Lechuga et al., Sensors and Actuators, B.8, pp. 249–252, 1992.

*Conductive–Oxide–Gate FET as a Gas Sensor,* L. I. Popova et al., Sensors and Actuators, B.3, pp. 273–277, 1991.

*Physics With Catalytic Metal Gate Chemical Sensors,* I. Lundström et al., vol. 15, Issue 3, pp. 201–278, 1989.

*Sensor Applications for Synthetic Polycrystalline Thin–Film Diamond,* T. Roppel et al., Sensors and Materials, 2,6, pp. 329–346, 1991.

*Thin Film Diamond Microstructures,* T. Roppel et al., Thin Solid Films, 212, pp. 56–62, 1992.

*Polycrystalline Diamond Device Processing,* C. D. Ellis et al., IEEE, pp. 222–225, 1991.

*Miniaturized Radiation Detector with Custom Synthesized Diamond Crystal Sensor,* J. H. Grobbelaar et al., Nuclear Instruments and Methods in Physics Research B61, pp. 553–559, 1991.

*Piezoresistivity in Vapor–Deposited Diamond Films,* M. Aslam et al., Appl. Phys. Lett., vol. 60, No. 23, pp. 2923–2925, Jun. 8, 1992.

*Diamond Electronics: Sparkling Potential,* I. Peterson, Science News, vol. 130, p. 118, 1986.

*Improved Tellurium Films by partially Ionized Vapor Deposition as the Semiconductor Layer of a TFT and a Hydrogen Sensor,* K. Okuyama et al., Japanese Journal of Applied Physics, vol. 28, No. 5, pp. 770–775, May, 1989.

*Diamond–Like Films as a Protecting Insulator for Gas–Detecting Suspended–Gate field Effect Transistor,* H. Lorenz et al., Surface and Coatings Technology, 47, pp. 746–753, 1991.

*Proceedings of the Conference on Recent Advances in Adaptive and Sensory Materials and Their Applications,* C. A. Rogers et al., Center for Intelligent Material Systems and Structures, Virginia Polytechnic Institute and State University, Apr. 27–29, 1992, pp. 254–265.

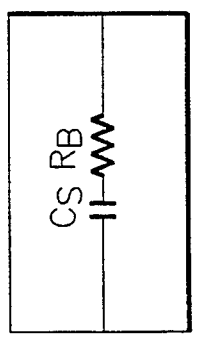
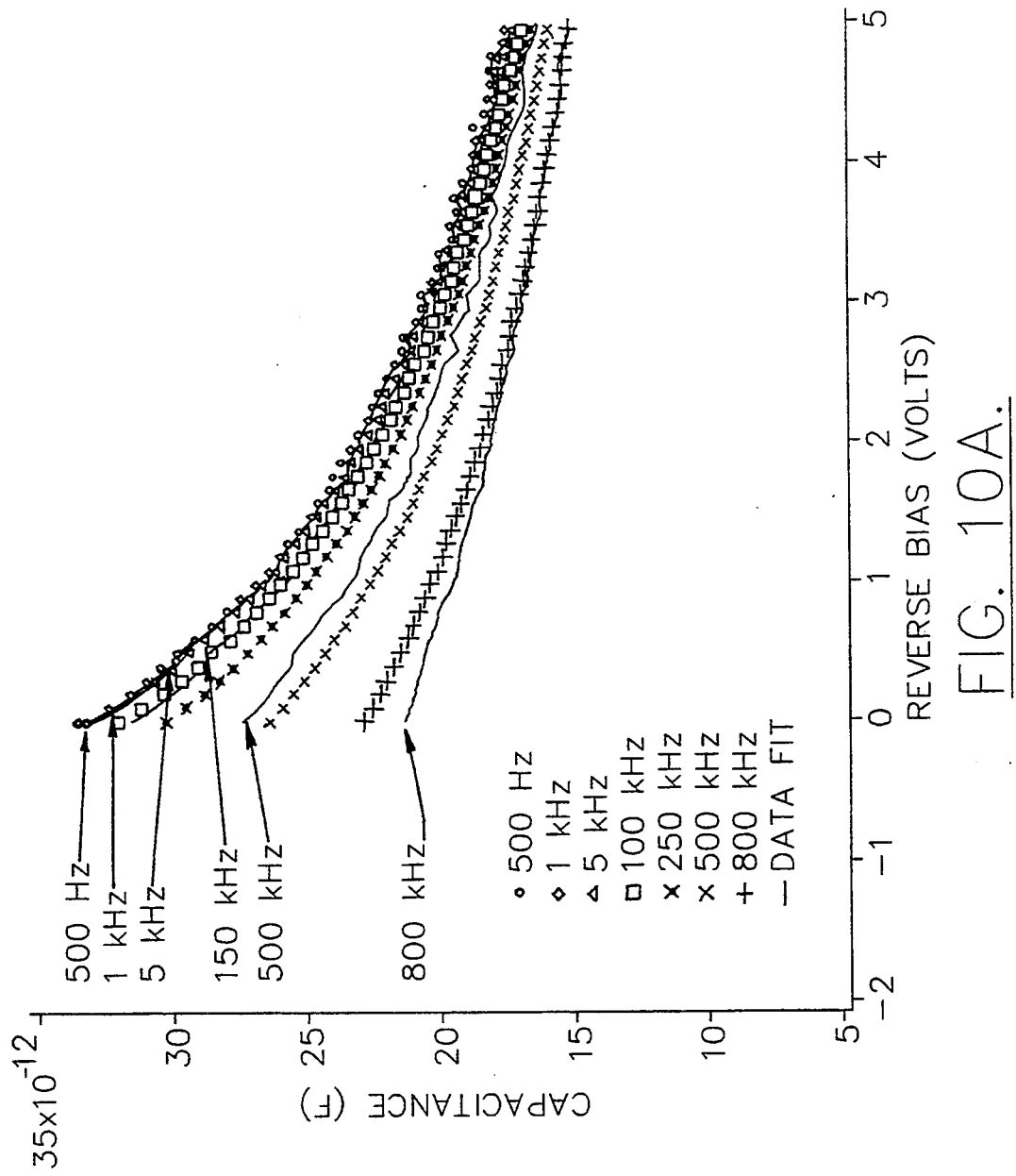

DIAMOND-BASED CHEMICAL SENSORS

CROSS REFERENCE TO RELATED APPLICATION

This application is a continuation-in-part of copending application Ser.No. 07/939,446 filed Sep. 2, 1992 now U.S. Pat. No. 5,285,034, issued Feb. 8, 1994.

FIELD OF THE INVENTION

This invention relates to microelectronic devices, and more particularly to microelectronic devices fabricated of diamond.

BACKGROUND OF THE INVENTION

Chemical sensors are widely used in industrial environments for process control, environmental control, and other applications. As is well known to those having skill in the art, a chemical sensor is a device which monitors the concentration of a given chemical species in a liquid or a gas. Chemical sensors are often required to be highly sensitive, in order to detect small concentrations of the chemical. They are also often required to withstand harsh chemical environments and/or high temperatures which may be present in process control, environmental control or other applications.

One form of chemical sensor is a gas sensor. Schottky diodes are widely used as gas sensors. As is well known to those having skill in the art, a diode exhibits a very low resistance to current flow in one direction and a very high resistance to current flow in the opposite direction, thereby producing current rectification. As is also well known to those having skill in the art, a Schottky diode produces rectification as a result of nonlinear current transport across a metal-semiconductor contact.

For example, a Schottky diode using a catalytic metal contact such as platinum or palladium, has been shown to be an excellent hydrogen gas sensor. In a Schottky diode, the Schottky barrier height decreases when the device is exposed to a hydrogen containing atmosphere. The hydrogen induced changes are typically detected as a modification of the capacitance voltage (C-V) or the current voltage (I-V) characteristics of the diode. See, for example, a publication entitled *Use of the Electroreflectance Technique in Pt/GaAs Schottky Barrier Sensor Characterization* by Lechuga et al., Sensors and Actuators, Vol. 32, pp. 354–356, 1992.

Diamond is a preferred material for semiconductor devices because it has semiconductor properties that are better than silicon, germanium or gallium arsenide. Diamond provides a higher energy bandgap, a higher breakdown voltage and a higher saturation velocity than these traditional semiconductor materials.

These properties of diamond yield a substantial increase in projected cutoff frequency and maximum operating voltage compared to devices fabricated using silicon, germanium or gallium arsenide. Silicon is typically not used at temperatures higher than about 200° C. and gallium arsenide is not typically used above 300° C. These temperature limitations are caused, in part, because of the relatively small energy band gaps for silicon (1.12 eV at ambient temperature) and gallium arsenide (1.42 Ev at ambient temperature). Diamond, in contrast, has a large band gap of 5.47 Ev at ambient temperature, and is thermally stable up to about 1400° C.

Diamond has the highest thermal conductivity of any solid at room temperature and exhibits good thermal conductivity over a wide temperature range. The high thermal conductivity of diamond may be advantageously used to remove waste heat from an integrated circuit, particularly as integration densities increase. In addition, diamond has a smaller neutron cross-section which reduces its degradation in radioactive environments, i.e., diamond is a "radiation-hard" material.

Because of the advantages of diamond as a material for semiconductor devices, there is at present an interest in the growth and use of diamond Schottky diode gas sensors. Unfortunately, it has been found that Schottky diodes fabricated from diamond exhibit frequency dependence of their capacitance/voltage characteristic, thereby limiting the usefulness of diamond based Schottky diodes and gas sensors.

The frequency dependent variation of the capacitance/voltage characteristic of diamond based Schottky devices has been widely investigated. See, for example, the publications entitled *The C-V Characteristics of Schottky barriers on Laboratory Grown Semiconducting Diamonds* by Glover, Solid State Electronics, Vol. 16, pp. 973–983 (1973); and *Electrical Characteristics of Schottky Diodes Fabricated Using Plasma Assisted Chemical Vapor Deposited Diamond Films* by Gildenblat et al., Applied Physics Letters, Vol. 53, No. 7, pp. 586–588 (1986).

In these investigations, the frequency dependent variation in capacitance/voltage characteristic has been attributed to the presence of deep level states in the diamond band gap, and to the high resistivity of bulk diamond as a result of diamond's unique energy level structure. Accordingly, characterizations of Schottky contacts have heretofore assumed that the undesirable frequency dependence of the capacitance/voltage characteristic was as a result of the inherent energy level structure (i.e. the deep level states in the diamond bandgap) and high series resistance of the diamond material itself. This undesirable frequency dependence limits the usefulness of diamond based gas sensors, notwithstanding the advantages of diamond as a material for semiconductor devices, especially in high frequency or fast transient applications.

SUMMARY OF THE INVENTION

It is therefore an object of the invention to provide diamond-based chemical sensors.

It is another object of the invention to provide diamond-based chemical sensors which exhibit reduced frequency dependence of their capacitance/voltage characteristic.

These and other objects are provided, according to the present invention, by a chemical sensor which includes a diode or a transistor fabricated in diamond. A diamond based diode chemical sensor includes a first diamond layer of first conductivity type and a second semiconductor layer of second conductivity type on the first diamond layer. The first and second layers form a semiconductor junction therebetween. The second layer may be a second diamond layer. At least one of the first and second layers is configured to allow a chemical which is external to the sensor to interact with the first or second layer and alter an electrical characteristic of the semiconductor junction. For example, at least one of the first and second layers is configured to allow absorption/adsorption of gas molecules or atoms, resulting in a change in the surface potential, conductivity, charge density or other characteristic. These changes may be detected by detecting shifts in the capacitance voltage (C-V) characteristics of the diode.

In a particular embodiment of a diamond based diode chemical sensor, the first diamond layer is a P-type diamond layer and the second layer includes an N-type gas sensitive second diamond layer. The second layer can also be an N-type moisture sensitive second layer, an N-type gas sensitive semiconducting oxide layer, an N-type carbon layer or another N-type chemical sensitive layer. Preferably, the first diamond layer is relatively lightly doped and an electrical contact is formed on the first diamond layer. A relatively highly doped region is formed in the first diamond layer, adjacent the electrical contact, so that the electrical contact forms an ohmic contact with the highly doped region. When the diamond layer includes a highly doped region adjacent the ohmic contact, the frequency dependence of the capacitance/voltage characteristic is reduced significantly.

A diamond based transistor chemical sensor includes a diamond layer and a field effect or bipolar transistor in the diamond layer. The transistor includes a controlling electrode, such as a gate or base electrode and first and second controlled electrodes such as source and drain electrodes or emitter and collector electrodes. The controlling electrodes are configured to allow a chemical external to the diamond based transistor to interact with the controlling electrode or the diamond layer, and alter the characteristics of the transistor. For example, the controlling electrode may include a gas sensitive or moisture sensitive layer. As also described above, a highly doped diamond layer is preferably formed adjacent the controlled electrodes (such as the source and drain) to form ohmic contacts and thereby reduce the frequency dependence of the capacitance/voltage characteristic of the transistor.

According to another aspect of the invention, the diamond based diode or transistor chemical sensor includes a heater which is thermally coupled to the sensor for heating the sensor to a predetermined temperature. Since diamond is capable of operating effectively at high temperatures, the heater may be provided to increase the chemical sensitivity of the sensor by elevating the temperature of the sensor. The heater can also be used to purge the chemical sensor or to move the sensor between operating temperatures to enhance sensitivity to different chemical species. A temperature monitor is also preferably coupled to the sensor for monitoring the temperature of the sensor. An accurate indication of the sensing temperature is thereby obtained. Preferably, the heater is an interdigitated resistive heater which is formed in one of the diamond layers of the diode or transistor, and the temperature monitor is preferably a diamond-based thermistor.

Diamond-based diode or transistor chemical sensors according to the present invention may operate in high temperature environments, in which conventional chemical sensors may not operate. They may also operate in corrosive environments in which conventional sensors may not operate without extensive encapsulation and other protection. Moreover, because they are based on diamond semiconductor, they can be integrated with transistors and other devices to form control or other circuits used with the chemical sensor.

According to another aspect of the invention, a diamond-based gas sensor includes a diamond layer having a Schottky contact thereon and an ohmic contact thereon, wherein the diamond layer includes a highly doped region adjacent the ohmic contact to provide a low resistance ohmic contact. It has been found, according to the invention, that the frequency dependence of the capacitance/voltage characteristic of gas sensors formed thereby is not primarily related to the presence of deep level states in the diamond band gap, as has been assumed for a period of over twenty years. Rather, according to the invention, it has been found that the strong frequency dependence is primarily a result of the high impedance (i.e. resistance and capacitance) of the "ohmic" contact which is typically applied to the diamond layer. The high series resistance of diamond also plays an important role in the frequency dependence, as has already been known. When the diamond layer includes a highly doped region adjacent the ohmic contact, the frequency dependence of the capacitance/voltage characteristic is reduced significantly. Gas sensors with improved operational characteristics are thereby provided.

According to the invention, the highly doped region adjacent the ohmic contact is preferably boron doped at a concentration of at least $10^{20}$ cm$^{-3}$. This doping forms an ohmic contact with a contact resistance of less than $10^{-3}$ $\Omega$-cm$^2$. Preferably, the ohmic contact is a back contact on a face of a diamond layer opposite the Schottky contact.

The diamond layer of the present invention can be a monocrystalline diamond layer or a polycrystalline diamond layer. The diamond layer may itself be formed on a diamond or a nondiamond substrate using techniques well known to those having skill in the art. When a back ohmic contact is formed on the diamond layer, a portion of the substrate is preferably removed to expose the back face of the diamond layer, opposite the Schottky contact, and allow the highly doped boron region to be formed. A metal contact is formed on the boron doped region.

The highly doped boron region can be formed in the diamond layer by in situ boron doping or boron ion implantation using techniques well known to those having skill in the art. By providing a highly doped boron layer adjacent the ohmic contact, frequency variations of the capacitance/voltage characteristics are reduced.

A gas sensor according to the invention includes a diamond layer having first and second opposing faces, and a first contact on the first face, wherein the first contact forms a Schottky barrier of predetermined Schottky barrier height between the first contact and the first face. The first contact allows gas to interact with the first face, to thereby alter the predetermined Schottky barrier height. The contact is preferably a catalytic metal contact such as platinum or palladium, which is sufficiently thin to allow gas to interact with the diamond layer. Preferably the catalytic metal layer is less than 1000 $\Omega$ thick. When the diamond layer is a layer of polycrystalline diamond, a layer of undoped diamond or a thin layer of silicon dioxide is also preferably included between the metal layer and the polycrystalline diamond layer. The gas sensor also includes a second contact, preferably on the second face, and the diamond layer includes a highly doped region, preferably boron doped at a concentration of at least $10^{20}$ cm$^{-3}$, adjacent the second contact, to form an ohmic contact having a contact resistance of less than $10^{-3}$ $\Omega$-cm$^2$. An improved gas sensor is thereby provided.

BRIEF DESCRIPTION OF THE DRAWINGS

FIGS. 10A and 10B are a graphical illustration of Capacitance-Voltage measurements as a function of frequency for a Schottky diode according to the present invention, and an equivalent circuit for a Schottky diode according to the present invention, respectively.

DESCRIPTION OF THE PREFERRED EMBODIMENTS

Figure 1:
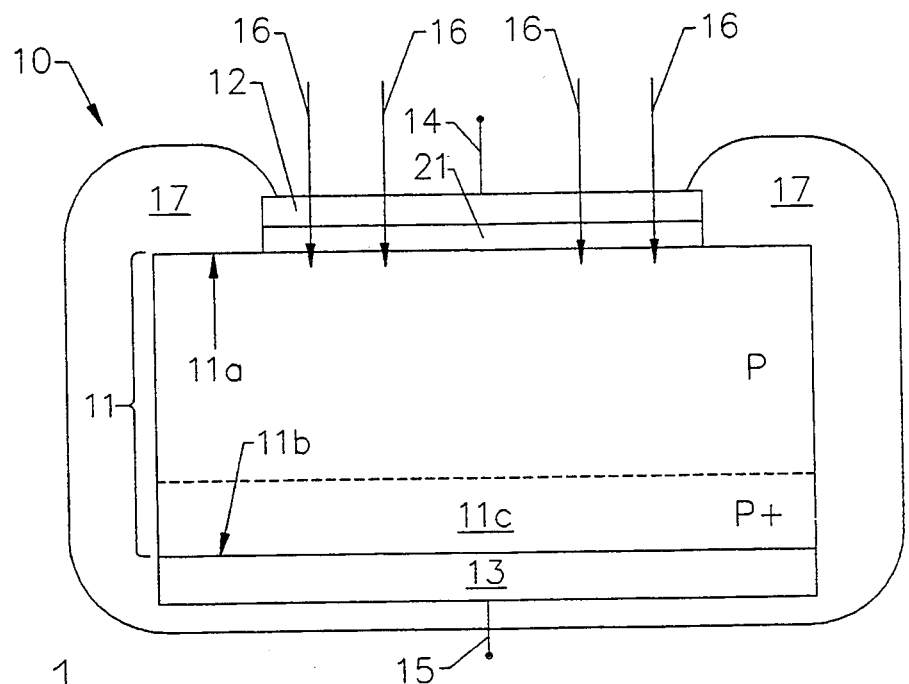
FIG. 1 illustrates a cross-sectional view of a first embodiment of a gas sensor according to the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thickness of layers and regions and positions of grain boundaries are exaggerated for clarity. Like numbers refer to like elements throughout.

Referring now to FIG. 1, a first embodiment of a diamond gas sensor according to the present invention is shown. Gas sensor 10 includes a diamond layer 11, preferably between about 1 $\mu$m and about 250 $\mu$m thick, and which is lightly doped, preferably at a boron concentration of $10^{15}$–$10^{18}$ atoms $cm^{-3}$. Diamond layer 11 may be a monocrystalline diamond layer or a polycrystalline diamond layer and may be formed using techniques well known to those having skill in the art. Diamond layer 11 includes a first face 11a and a second face 11b. Other high bulk resistance semiconductors, such as silicon carbide or gallium nitride may be used.

As also shown in FIG. 1, diamond layer 11 includes a highly doped region 11c at second face 11b. Layer 11c is preferably between about 0.3 $\mu$m and about 1 $\mu$m thick and is heavily doped with boron at $10^{20}$–$10^{21}$ atoms $cm^{-3}$ to produce a P++ region.

Still referring to FIG. 1, a Schottky contact 12 is formed on first face 11a of diamond layer 11. Schottky contact 12 is formed of a metal which forms a Schottky barrier with diamond. Schottky contact 12 is preferably formed of a catalytic metal such as platinum or palladium. The catalytic metal allows the sensing gas to rapidly pass therethrough in a direction shown by arrows 16 and interact with the first face 11a of diamond layer 11. Schottky contact 12 is preferably sufficiently thin to allow the gas to interact with the diamond layer. When platinum or palladium is used, a thickness of less than about 100 Å is preferred.

As described above, diamond layer 11 may be a monocrystalline diamond layer or a polycrystalline diamond layer. When a monocrystalline diamond layer is used, the Schottky contact 12 is typically formed directly on the first face 11a of monocrystalline diamond layer 11. However, when a polycrystalline diamond layer is used, a Schottky contact is preferably formed by including an intermediate layer 21 between the metal 12 and the polycrystalline diamond layer 11. This intermediate layer is preferably a layer of undoped (insulating) diamond, about 2000 Å thick, as described in the publication by Miyata et al. entitled *Metal-Intrinsic Semiconductor-Semiconductor Structures Using Polycrystalline Diamond Films*, Applied Physics Letters, Vol. 60, No. 4 (1992), pp. 480–482. Alternatively, intermediate layer 21 may be a very thin layer of silicon dioxide ($SiO_2$), about 20 Å thick, between metal layer 12 and polycrystalline diamond layer 11, as described in a publication by coinventor V. Venkatesan et al. entitled *Effect of Thin Interfacial $SiO_2$ Films on Metal Contacts to B-Doped Diamond Films*, Journal of the Electrochemical Society, Vol. 139, No. 5 (1992), pp. 1445–1449.

As is well known to those having skill in the art, the gas which enters substrate 11, as shown by arrows 16, alters the barrier height of the Schottky barrier formed between contact 12 and face 11a. This change in barrier height is used as a criteria for detecting the gas, using techniques well known to those having skill in the art. Heretofore, the frequency dependence of the capacitance of the Schottky contact was a strong influence in the determination of barrier height. It was thought that this frequency dependence was due to the presence of deep level states in the diamond band gap and to the high resistivity of the diamond layer 11. Accordingly, the inherent characteristics of diamond itself were heretofore thought to be limiting factor in the performance of gas sensors.

According to the invention, an ohmic contact is formed of metal 13 on the second face 11b of diamond layer 11, adjacent the highly doped region 11c. The highly doped region preferably produces a contact resistance of less than $10^{-3}$ $\Omega$-$cm^2$. A first and second electrode 14 and 15 respectively, connect the Schottky contact 12 and ohmic contact 13 respectively. Suitable encapsulation 17 is used to protect the device, while allowing gas to interact with the diamond layer 11 at the first face and thereby altering the Schottky barrier height. It will be understood by those having skill in the art that suitable encapsulation 17 may also be provided on Schottky contact 12 for protective purposes, as long as gas interaction is still provided.

Figure 2:
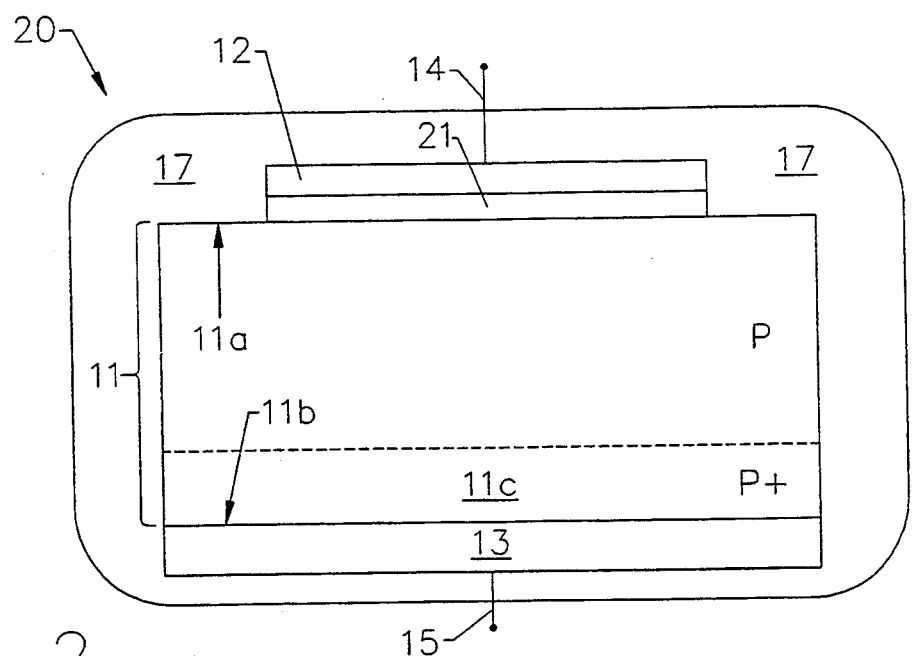
FIG. 2 illustrates a cross-sectional view of a first embodiment of a Schottky diode according to the present invention.

Referring now to FIG. 2, a first embodiment of a Schottky diode 20 according to the invention is shown. This embodiment is similar to the gas sensor 10 shown in FIG. 1, except that the encapsulation 17 prevents penetration of ambient gases into diamond layer 11. Layer 12 is also preferably at least 2000 Å thick.

Figure 3:
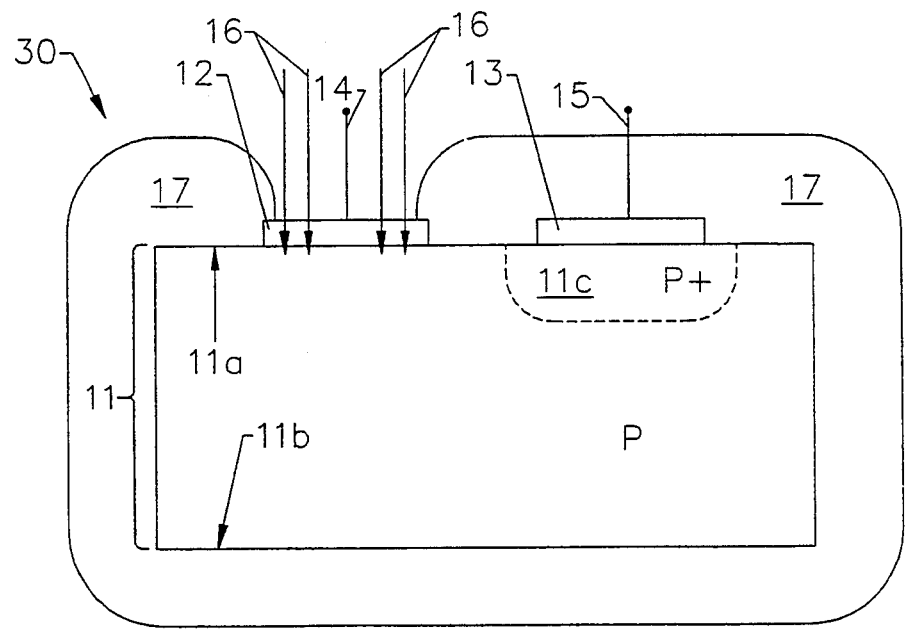
FIG. 3 illustrates a cross-sectional view of a second embodiment of a gas sensor according to the present invention.
Figure 4:
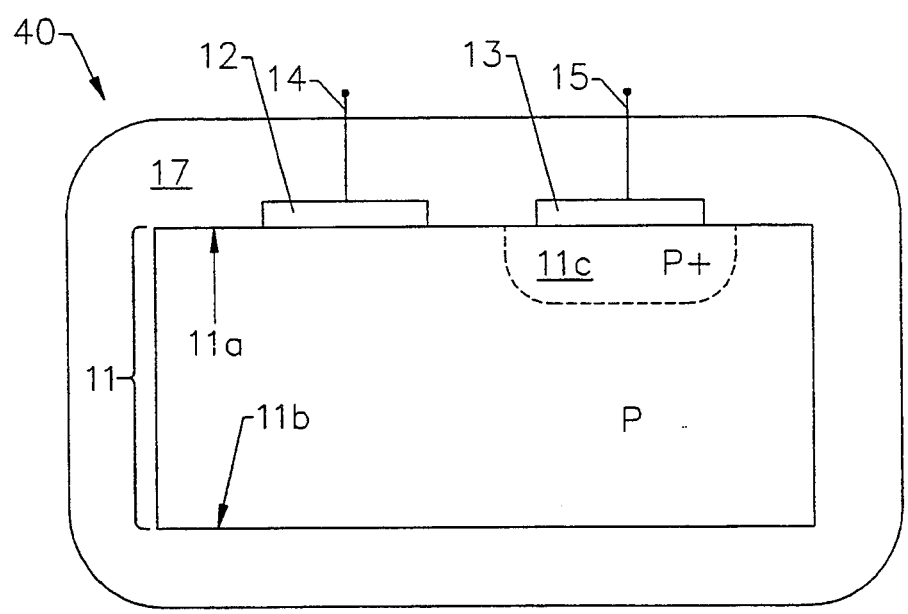
FIG. 4 illustrates a cross-sectional view of a second embodiment of a Schottky diode according to the present invention.

FIG. 3 illustrates a second embodiment of a gas sensor according to the present invention. As shown in FIG. 3, gas sensor 30 includes both an ohmic contact 13 and a Schottky contact 12 on the first face 11a of the diamond layer 11. Accordingly, heavily doped region 11c is formed at first face 11a adjacent ohmic contact 13. FIG. 4 illustrates a second embodiment of a Schottky diode 40 including Schottky contact 12 and ohmic contact 13 at the first face 11a of the diamond substrate. In the embodiments of FIGS. 3 and 4, it is assumed that layer 11 is monocrystalline diamond, so that layer 21 is not shown.

The Schottky diodes and gas sensors of FIGS. 1–4 can be fabricated by using natural (type IIb) diamond crystals 11 which are polished and chemically cleaned in $CrO_3 + H_2SO_4$ acid solution followed by cleaning in aqua regia ($3HCl + 1HNO_3$) and RCA solutions. Platinum or palladium films are formed on the first surface 11a of the diamond crystal 11 using a well known resistance heating technique. Region 11c may be formed by ion implanting the second face 11b (FIG. 1 or FIG. 2) or the first face 11a (FIG. 3 or FIG. 4) of diamond layer 11, as appropriate, with boron. The implantation dose is preferably $5 \times 10^{16}$ $cm^{-2}$ at an energy of 60 keV and a target temperature of 200° C. The diamond crystals are then annealed in a furnace at about 1200° C. for 30 minutes at $1 \times 10^{-7}$ Torr. The graphite formed during implantation and annealing is then etched in $CrO_3 + H_2SO_4$ acid solution at about 200° C. A high atomic boron concentration at the appropriate surface 11a (FIG. 1 or FIG. 2) or 11b (FIG. 3 or FIG. 4) of $10^{20}$–$10^{21}$ $cm^{-3}$ is obtained.

Then, metal contact 13 is formed using a refractory metal, preferably titanium, about 200 Å to about 400 Å thick. Other refractory metals may also be used. A gold passivating layer, preferably about 1000 Å to about 1500 Å thick may then be formed on the refractory metal layer. Other passivating layers may also be used. An anneal may then be performed at about 800° C. to about 850° C. for a time period of about fifteen minutes to about ninety minutes, to convert at least a portion of the titanium layer to titanium carbide. A low resistance source contact is thereby formed. The process for forming the ohmic contact layer 13 is similar to the process for forming ohmic contacts on diamond as described by Moazed et al. in *A Thermally Activated Solid State Reaction Process for Fabricating Ohmic Contacts to Semiconducting Diamond*, Applied Physics Journal, Vol. 68, No. 5, September 1990.

Figure 5:
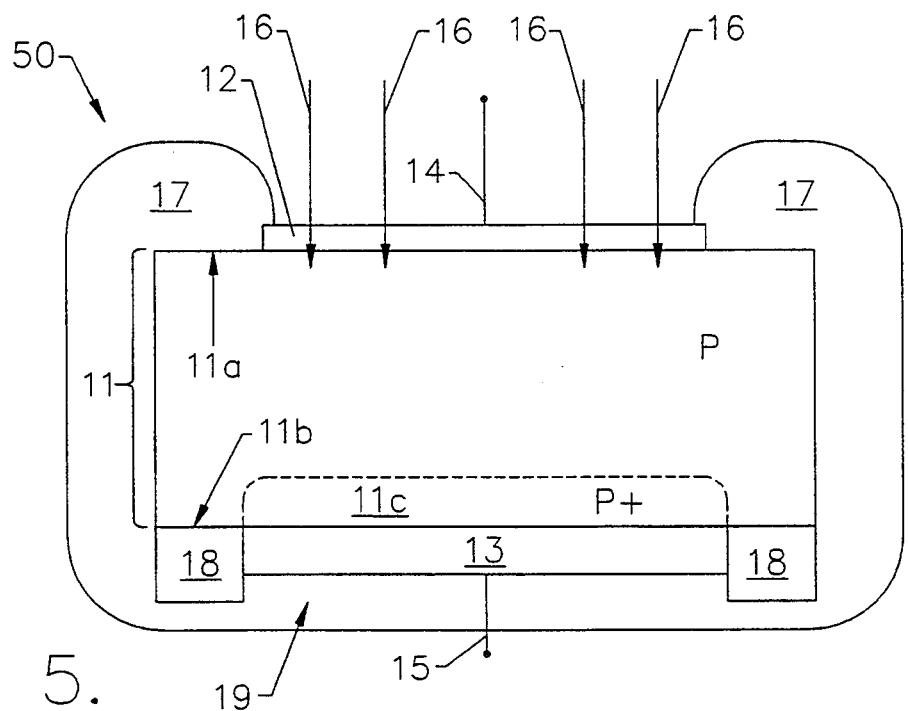
FIG. 5 illustrates a cross-sectional view of a third embodiment of a gas sensor according to the present invention.

Referring now to FIG. 5, a third embodiment of the gas sensor according to the invention is described. Gas sensor 50 is similar to gas sensor 10 described in FIG. 1 except that diamond layer 11 is itself formed on a substrate 18. The substrate 18 may be a diamond substrate or a nondiamond substrate. To facilitate formation of a monocrystalline diamond layer 11, substrate 18 is preferably crystalline silicon carbide, cubic boron nitride, crystalline copper or crystalline nickel. Alternatively, substrate 18 may be a diamond substrate. A polycrystalline diamond layer 11 may also be grown on a nondiamond or diamond substrate using techniques well known to those having skill in the art. If a polycrystalline diamond layer 11 is used, layer 21 is also preferably present, as was described above.

Figure 6:
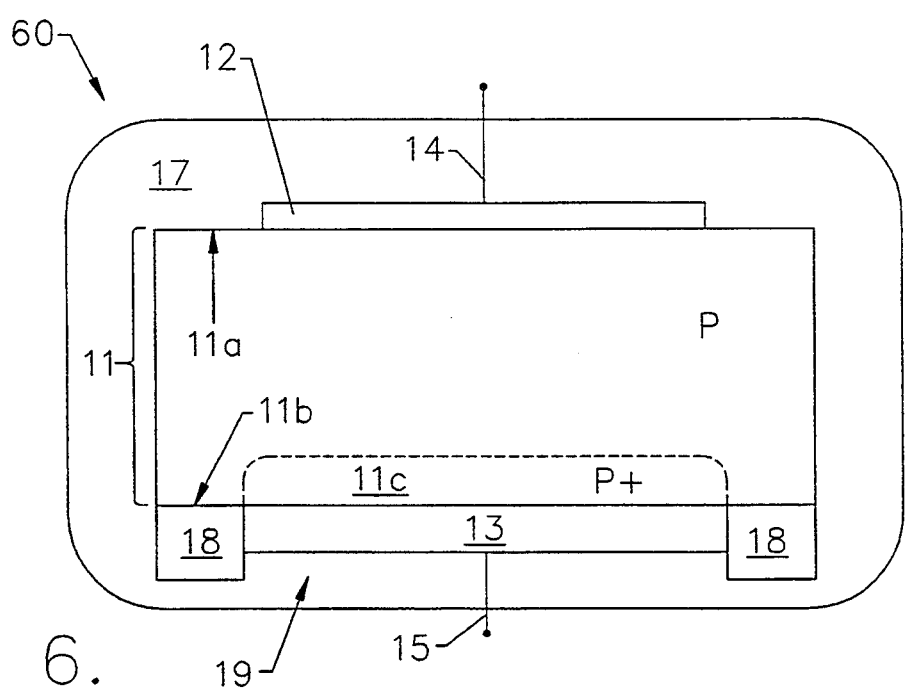
FIG. 6 illustrates a cross-sectional view of a third embodiment of a Schottky diode according to the present invention.

As shown in FIG. 5, a portion of substrate 18 is removed to form an aperture 19 therein about 2 mm in diameter, to allow access to back face 11b of diamond layer 11. A heavily doped boron region 11c is formed by implantation through the aperture 19. An ohmic contact 13 is then formed as was already described. FIG. 6 illustrates a similar configuration of a Schottky diode 60 having an implanted region 11c on the back face 11b of diamond layer 11.

Figure 7:
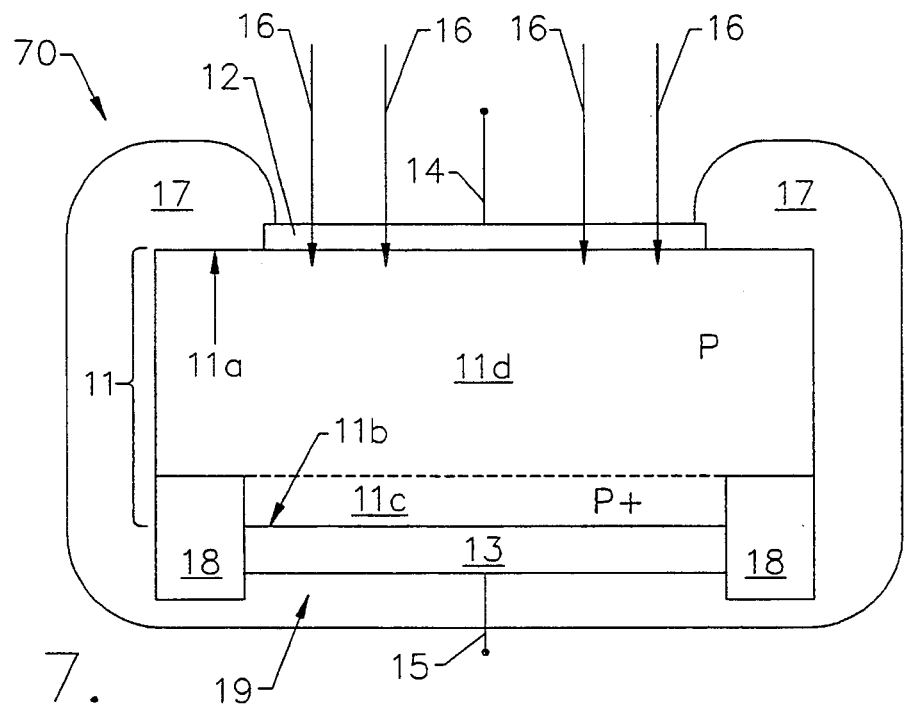
FIG. 7 illustrates a cross-sectional view of a fourth embodiment of a gas sensor according to the present invention.
Figure 8:
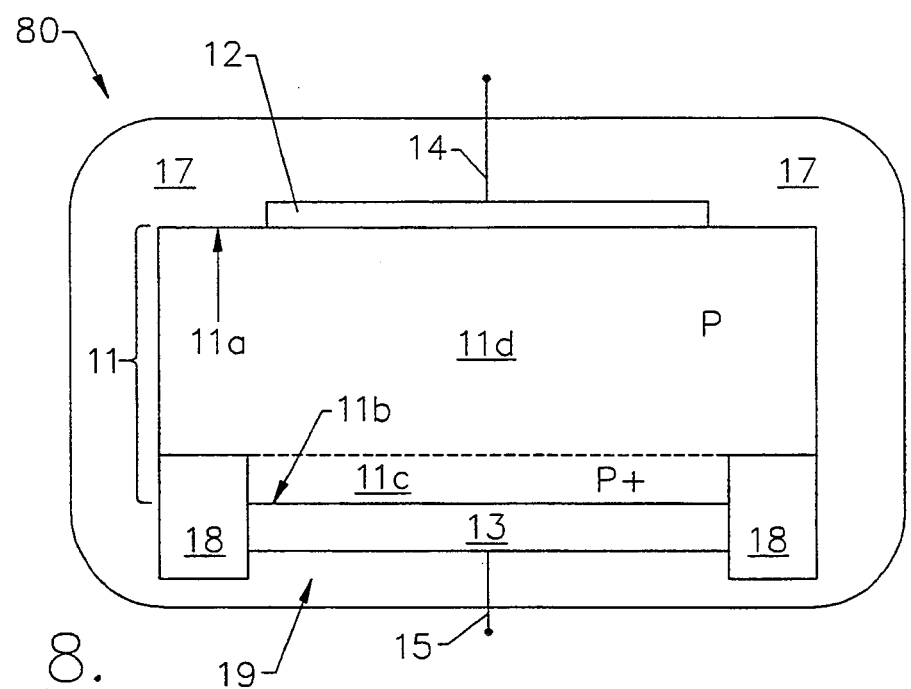
FIG. 8 illustrates a cross-sectional view of a fourth embodiment of a Schottky diode according to the present invention.

Referring now to FIG. 7, yet another embodiment of a diamond based gas sensor 70 according to the present invention is shown. In this embodiment, heavily doped region 11c is grown on lightly doped portion 11d using in situ doping through the aperture 19. An in situ doped region having thickness of between about 0.3 μm and about 1 μm is formed. FIG. 8 illustrates a Schottky diode 80 formed using an in situ doped heavily born doped region 11c as described in connection with FIG. 7.

According to the invention, heavily doped boron layer 11c, in combination with contact 13 provides a low resistance ohmic contact. The low resistance ohmic contact dramatically reduces the frequency dependence of the measured capacitance of a diamond Schottky diode and diamond gas sensor. This strong frequency dependence of the measured capacitance was heretofore assumed to result from the inherent properties of the diamond itself, i.e. deep level states and series resistance. According to the invention, by providing a low contact resistance ohmic contact for the Schottky diode and gas sensor, improved device performance may be obtained.

In order to compare the performance of a Schottky diode with and without the ohmic contact of the present invention, natural (type IIb) diamond crystals were polished and chemically cleaned in $CrO_3+H_2SO_4$ acid solution, followed by cleaning in aqua regia ($3HCl+1HNO_3$) and RCA solutions. Aluminum (Al) and Platinum (Pt) films (about 2000 Å in thickness) were deposited on two different cleaned diamond crystals using a resistance heating technique. A molybdenum mask, with 355.6 μm diameter holes, was used during deposition to define metal dots on the diamond crystals. In order to study the effect of back contact resistance on capacitance/voltage (C-V) characteristics, the backside of some of the crystals were boron (B) ion implanted to achieve a high B concentration region 11c at the surface. The implantation conditions were as follows: Dose—$5 \times 10^{16}$ cm$^{-2}$; Energy—60 keV; Target temperature—200° C. The crystals were then annealed in a furnace at 1200° C. for 30 min at $1 \times 10^{-7}$ Torr. The graphite formed during implantation and annealing was etched in $CrO_3+H_2HO_4$ acid solution at abut 200° C. A high atomic B concentration at the second surface 11b of $10^{20}$–$10$<cm$^{-3}$ was obtained.

Electrical measurements were performed on the contacts in a vertical configuration after mounting the samples on a platinum plate using silver paste, with the silver paste contacting region 11b (no ohmic contact) or 11c (ohmic contact). Current-voltage (I-V) measurements were performed using an HP4145B semiconductor parameter analyzer. An HP4284A LCR meter was used to perform the C-V measurements. The I-V characteristics of Al and Pt contacts showed excellent rectification. At an applied bias of 20 V, reverse leakage current densities of $4.1 \times 10^{-8}$ and $6.3 \times 10^{-9}$ A/cm$^2$ were obtained for Al and Pt contacts, respectively. The C-V measurements were performed in a parallel circuit mode because of the high impedance of metal/diamond Schottky junctions. The reliability of C-V measurements was evaluated by a quality factor Q, expressed as $Q=RC\omega$, where R is the equivalent parallel resistance and $\omega$ is the angular frequency. A value of $Q>5$ was considered to be a reliable measurement.

Figure 9B:
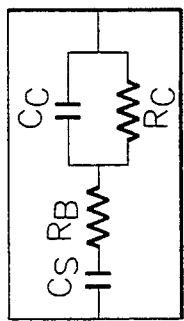
FIGS. 9A and 9B are a graphical illustration of Capacitance-Voltage measurements as a function of frequency for a conventional Schottky diode, and an equivalent circuit for the conventional Schottky diode, respectively.
Figure 9A:
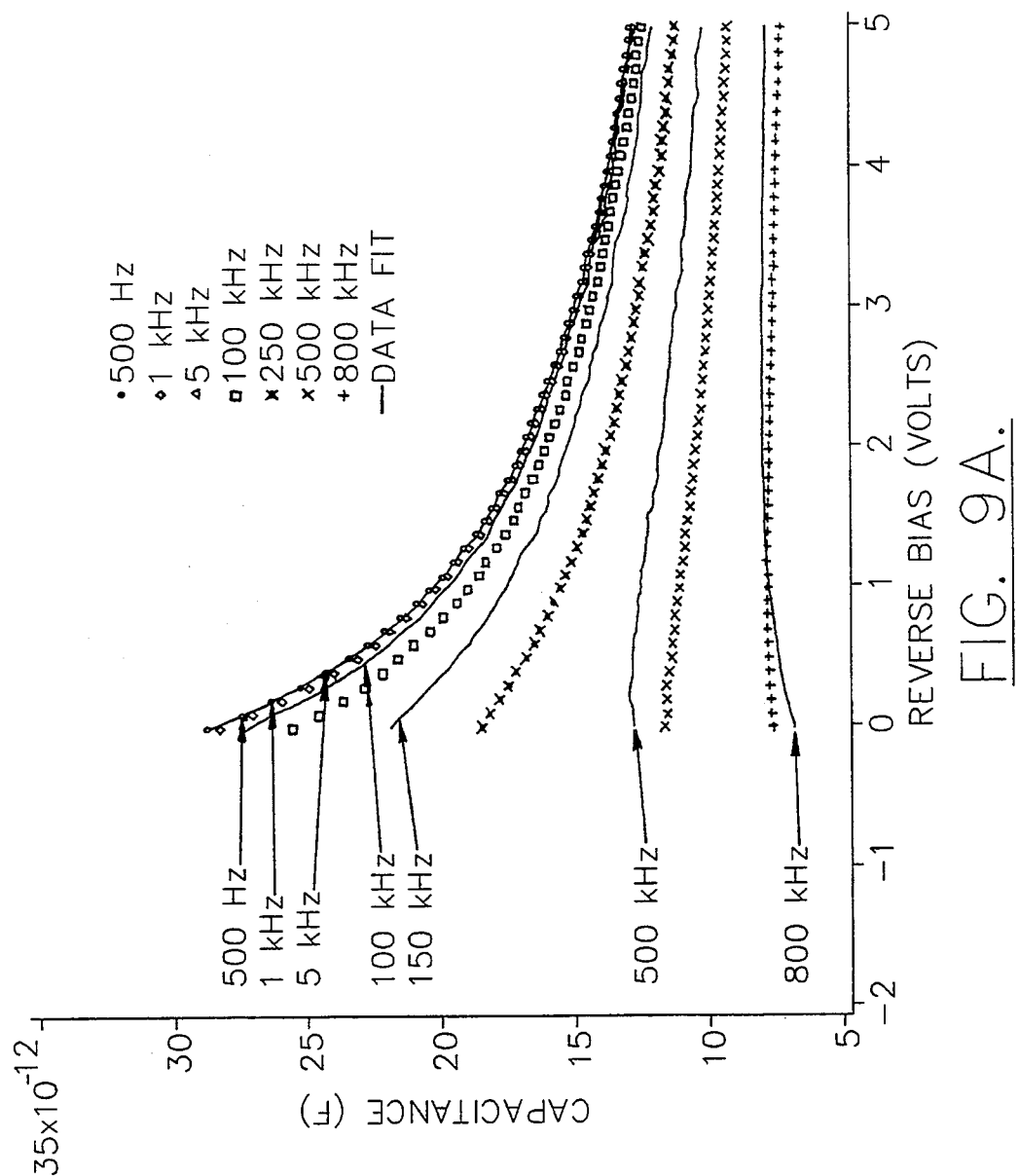

The C-V measurements as a function of frequency (500 Hz to 800 kHz) performed on Al/diamond structure before and after back side implantation are shown in FIGS. 9a and 10a, respectively. The frequency dependence of capacitance observed in FIG. 9a is minimized significantly in FIG. 10a. The heavily doped boron layer 11c dramatically reduces the frequency dependence of the C-V curves. Similar C-V curves were obtained for Pt contacts fabricated on another natural diamond before and after back side implantation. Plots of $1/C^2$ versus reverse bias voltage yielded straight lines for the entire bias and frequency range investigated. A linear least square fit through 1/C2-V for data in FIG. 10a at 500 Hz, yields a value of $2.9\pm0.2 \times 10^{16}$ cm$^{-3}$ for the dopant concentration and a value of $2.1\pm0.1$ eV for the barrier height. The corresponding values for Pt contacts on a similar natural diamond were $2.6\pm0.1 \times 10^{16}$ cm$^{-3}$ and $2.3\pm0.1$ eV.

The value for the dopant concentration is the uncompensated B concentration and is in agreement with other reported values. Secondary ion mass spectrometry (SIMS) analysis of a natural (type IIb) diamond showed an atomic B concentration of $\cong 1$–$5 \times 10^{16}$ cm$^{-3}$. This value agrees well with the ionized dopant concentration in the depletion region (obtained from C-V measurements) of the metal-diamond diodes investigated. Also, the Schottky barrier height is independent of the metal work function. This is believed to be due to Fermi level pinning.

An AC equivalent circuit shown in FIG. 10b has been used to model the C-V measurements shown in FIG. 10a. In this circuit, $C_s$ (F/cm$^2$) is the specific capacitance of the Schottky barrier, $R_B$ is the bulk resistance of diamond, $C_c$ (F/cm$^2$) is the specific contact capacitance and $R_c$ (Ω-cm$^2$) is the specific contact resistance. Measured capacitance, $C_m$ (F) of the device can be expressed as:

$$C_m = G_B A_S C_S \frac{G_B C_C + G_C C_S) + G_C(G_C G_B - \omega^2 C_C C_S)}{(G_C G_B - \omega^2 C_C C_S)^2 + \omega^2(C_C G_B + C_S R_a G_B + G_C C_S)^2} \quad (1)$$

where, $A_s$ (cm$^2$) is the Schottky contact area, $A_c$(cm$^2$) is the contact area, $G_C$ (S/cm$^2$) is the contact specific conductance, $G_B$ (S/cm$^2$) is the bulk specific conductance, $\omega$ is the angular frequency and $R_a=A_S A_C$. It can be seen from Equation 1 that, for low frequencies $C_m \cong A_S \cdot C_S$. Using this model, fits were made to the C-V data (solid lines), as shown in FIG. 9a. The fit to experimental data is reasonably good for all frequencies in the range 500 Hz to 800 kHz. It was assumed in the model that, $C_C$ and $G_C$ are not a function of voltage and/or frequency. $C_C$ and $G_C$ were measured by performing C-V and I-V measurements, respectively, on Ag/diamond structures with low resistance back contacts. The following values were used for the variables in the model; $G_B=7.2 \times 10^{-2}$ S/cm$^2$, $G_C=5.1 \times 10^{-6}$ S/cm$^2$, $A_s=9.9 \times 10^{-4}$ cm$^2$, $R_a=4 \times 10^{-3}$, $C_C=1.8 \times 10^{-9}$ F/cm$^2$. The values of $C_m$ as a function of bias at 500 Hz were assumed to be equal to $C_S$. The value of $G_B$ listed above corresponds to a bulk resistance of 14 kΩ. This value was in good agreement to the measured value of the bulk resistance of natural diamond.

The circuit, shown in FIG. 10b can be used to model the frequency dependence of C-V measurements on rectifying contacts to back side implanted diamond crystals according to the present invention. In this case, $C_m$ becomes:

$$C_m = (A_S C_S G_B^2)/(G_b^2 \omega^2 C_S^2) \quad (2)$$

It can be seen from Equation 2 that, for low frequencies, $C_m \cong A_S \cdot C_S$. Using this model, fits (solid lines) were made to the C-V data obtained from measurements on Al contacts with implanted back contact (FIG. 10a). It is observed that the fit to experimental data is reasonably good for all frequencies in the range 500 Hz to 800 kHz. As before, the values of $C_m$ as a function of bias at 500 Hz were assumed to be equal to $C_S$. A value of 0.23 S/cm$^2$ was used for $G_B$ in the model. This corresponds to a value of 4.3 kΩ for the bulk resistance of diamond.

In summary, differential capacitance-voltage (C-V) measurements were performed on Al and Pt rectifying contacts on natural (type IIb) diamonds. Capacitance-voltage data showed frequency dependence, which decreased significantly after reducing the back contact impedance. Accordingly, the frequency dependence of capacitance-voltage data seems primarily to be an effect of back contact capacitance and resistance, as well as the bulk resistance of diamond. High performance Schottky diodes and gas sensors are obtained.

Figure 11:
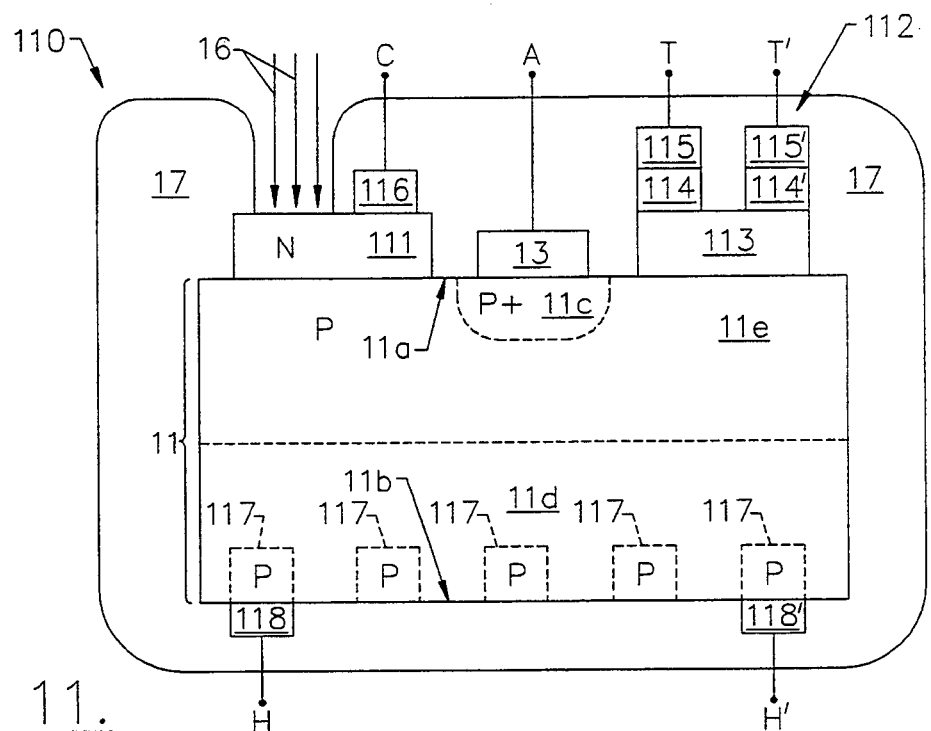
FIG. 11 illustrates a cross-sectional view of a first embodiment of a diamond-based diode chemical sensor according to the invention.

Referring now to FIG. 11, a first embodiment of a diamond based diode chemical sensor according to the invention is shown. Chemical sensor 110 includes a diamond layer 11 as was already described regarding previous embodiments. As shown, diamond layer includes a lightly doped region 11e preferably doped at a boron concentration of $10^{15}$–$10^{18}$ atoms cm$^{-3}$. An undoped region 11d preferably has a doping concentration of less than $10^{15}$ atoms cm$^{-3}$. A highly doped region 11c is also included at first face 11a. Region 11c is preferably heavily doped with boron at $10^{20}$–$10^{21}$ atoms cm$^{-3}$.

Still referring to FIG. 11, a diode is formed on first face 11a of diamond layer 11 by forming a chemical or gas sensitive semiconductor region of opposite conductivity type from region 11e, on first face 11a. For example, there are numerous gas sensitive oxides which may be used to make a heterojunction with P-type diamond resulting in a gas sensitive diode. See for example Tables 1 and 4 of the publication entitled *Materials Selection for Semiconductor Gas Sensors* by P. T. Moseley, Sensors and Actuators, Vol. B6, pp. 149–156 (1992), the disclosure of which is incorporated herein by reference. Table 1 and Table 2 below reproduce the characteristics of some of the materials described in the Moseley reference. Table 1 describes materials that can be used as oxygen sensors. Table 2 describes materials which can be used for other gas sensors.

TABLE 1

| Material | Sensing Temperature (°C.) |
|---|---|
| TiO$_2$ | 700–800 |
| Cr$_2$O$_3$ | 900 |
| Nb$_2$O$_5$ | 900 |
| CeO$_2$ | 900 |
| ThO$_2$ | 900 |
| Ga$_2$O$_3$ | 900 |
| SrMg$_x$Ti$_{1-x}$O$_{3-\delta}$ | 700 |
| SrTiO$_3$ | 700 |
| BaTiO$_3$ | 700 |
| BaFe$_{1-x}$M$_x$O$_{3-\delta}$ M = Ta, Nb, Ti, Zr, Hf, Sn | 700–900 |
| Ga$_2$O$_3$ | 1000 |
| ZnCr$_2$O$_4$ | 800 |

TABLE 2

| Material | Sensing Temperature (°C.) | Gas Responses |
|---|---|---|
| ZnO (Al doped) | 200 | H$_2$ |
| ZnO | 450 | CCl$_2$F$_2$, CHClF$_2$ |
| ZnO | 280–470 | CO |
| AnO (Al, In or Ga-doped) | 350 | NH$_3$ |
| WO$_3$ (Pt) | 350 | H$_2$, CH$_4$, C$_4$H$_{10}$ |
| WO$_3$ | 250–400 | N$_2$H$_4$, NH$_3$, H$_2$S |
| TiO$_2$ (Ru) | 500 | CO, CH$_4$, SO$_2$ |
| αFe$_2$O$_3$ | 560 | (CH$_3$)$_3$N |
| τFe$_2$O$_3$ | 400 | H$_2$, CH$_4$ |
| | 420 | H$_2$, CH$_4$, C$_3$H$_8$, C$_4$H$_{10}$, C$_2$H$_5$OH |
| CdIn$_2$O$_4$ | 300 | CO |
| NiTa$_2$O$_6$ | 100 | H$_2$, CO |
| CoTa$_2$O$_6$ | 100 | H$_2$, CO |
| CuTa$_2$O$_6$ | 400 | H$_2$, CO |
| BaTiO$_3$ (Ag) | 300 | CO |

TABLE 2-continued

| Material | Sensing Temperature (°C.) | Gas Responses |
|---|---|---|
| SrFeO$_{3-y}$ | 470 | CH$_4$ |
| Zn$_x$GeO$_y$N$_z$ | 200–300 | NH$_3$ |
| Cr$_2$O$_3$ (Ti) | 420 | (CH$_3$)$_3$N |
| In$_2$O$_3$ (Mg or Zn) | 420 | (CH$_3$)$_3$N |
| Bismuth molybdate | 330 | C$_2$H$_5$OH |
| Bismuth chromate | 270 | C$_2$H$_5$OH |
| BaSnO$_3$ | 300–500 | H$_2$, CO, CH$_4$, H$_2$S, SO$_2$ |
| Bi$_2$Sn$_2$O$_7$ | 500 | H$_2$, CO, C$_2$H$_4$, NH$_3$ |
| Bi$_6$Fe$_4$Nb$_6$O$_{30}$ | 500 | C$_3$H$_8$, Cl$_2$, NO$_2$, SO$_2$, H$_2$S |

Thus, for example, titanium dioxide may be used. As is well known to those having skill in the art, titanium dioxide exhibits N-type semiconductor characteristics at elevated temperatures in response to oxygen.

As can be seen from the above Tables, most of the gas sensitive oxides typically operate in the 200°–700° C. temperature range which is compatible with P-type diamond but incompatible with most other semiconductors. Alternatively, an all carbon PN-diode humidity sensor can be fabricated using a partially polycondensated furfuryl alcohol layer 111 which is deposited on the diamond substrate 11 at 400°–450° C. by spray pyrolysis followed by an annealing at 550°–800° C. to produce an N-type carbon layer 111 on the P-type diamond region 11e. See the publication by Lukaszewicz entitled *An Application of Carbon-Type Semiconductors for the Construction of a Humidity-Sensitive Diode*, Sensor Actuator, Vol. B6, pp. 61–65 (1992), the disclosure of which is hereby incorporated herein by reference.

As described above, many of the N-type gas sensitive or moisture sensitive layers operate best at elevated temperatures. Accordingly, in a preferred embodiment, the diamond-based diode sensor preferably includes an interdigitated resistive heater 117, preferably doped P-type, at a boron concentration of $10^{15}$–$10^{22}$ atoms cm$^{-3}$, in undoped diamond region 11d. The sensors of the present invention may incorporate a heater in order to operate at higher temperatures which may be optimal for sensitivity, or even a requirement for activation of the gas sensitive semiconductor. The heater can also be used to purge the surface if saturation occurs and can be used to move the device between operating temperatures where the gas sensitive semiconductor may be sensitive to different species.

Also preferably, in order to monitor and regulate the temperature, a temperature monitor 112 is also included, for example on first face 11a. Many configurations of temperature monitors may be included. One configuration uses doped diamond regions 114 (for example, boron doping concentration of about $1 \times 10^{17}$–$1 \times 10^{19}$ cm$^{-3}$) on an undoped diamond layer 113. However, it will be understood by those having skill in the art that other configurations of temperature monitors may be used. The resistive heater 117 and the temperature monitor 112 are thermally coupled to the diamond based diode sensor 110.

Appropriate metal or other contacts are also included for electrically contacting the respective regions of sensor 110. Contact 116 electrically contacts layer 111. Contact 13 electrically contacts P+ layer 11c. Contacts 115 and 115' electrically contact regions 114 and 114', and contacts 118 and 118' electrically contact resistive heater 117.

Finally, appropriate external connections are provided for the device. In particular, a cathode C, an anode A, a pair of temperature monitor connections T, T', and a pair of heater connections H, H' are provided. The device is also encapsulated by layer 17 as was already described in connection with previous embodiments. However, it will be understood by those having skill in the art that the use of diamond in the sensor may reduce or eliminate the need for encapsulation.

Figure 12:
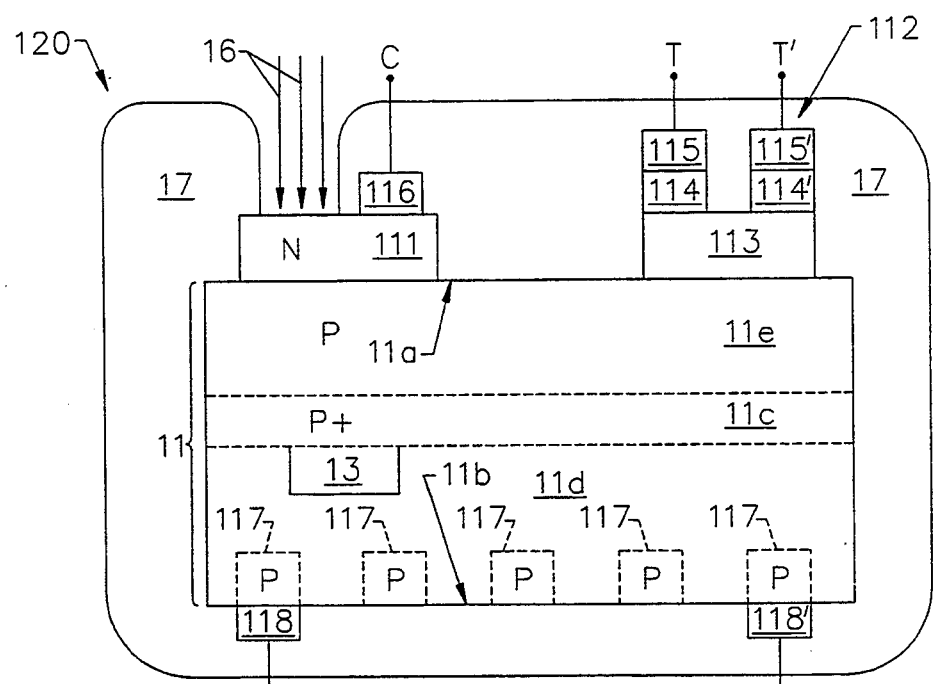
FIG. 12 illustrates a cross-sectional view second embodiment of a diamond-based diode chemical sensor according to the invention.
Figure 13:
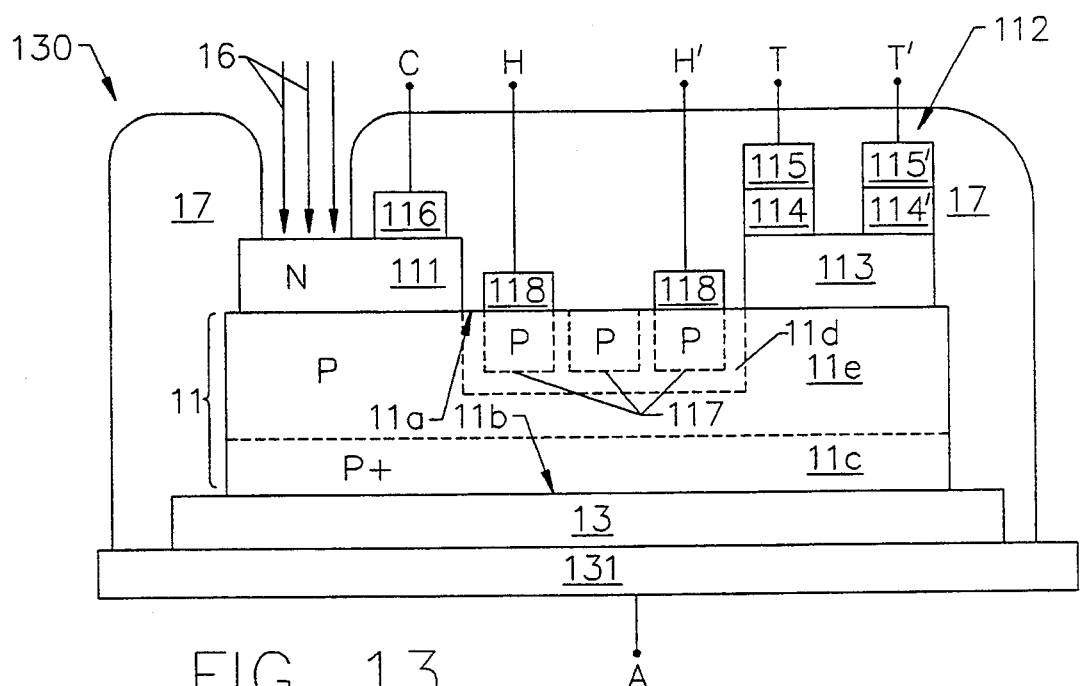
FIG. 13 illustrates a cross-sectional view of a third embodiment of a diamond-based diode chemical sensor according to the invention.

FIG. 12 illustrates a second embodiment of a diode based diamond chemical sensor. As shown, chemical sensor 120 includes a buried anode contact 13 with P+ layer 11c adjacent thereto. The remaining structure is similar to that described in FIG. 11. FIG. 13 illustrates a third embodiment of a diode based chemical sensor 130 in which the resistive heater 117 is at face 11a and the anode contact is at face 11b. The device is mounted on a substrate 131 such as a metal substrate.

Figure 14:
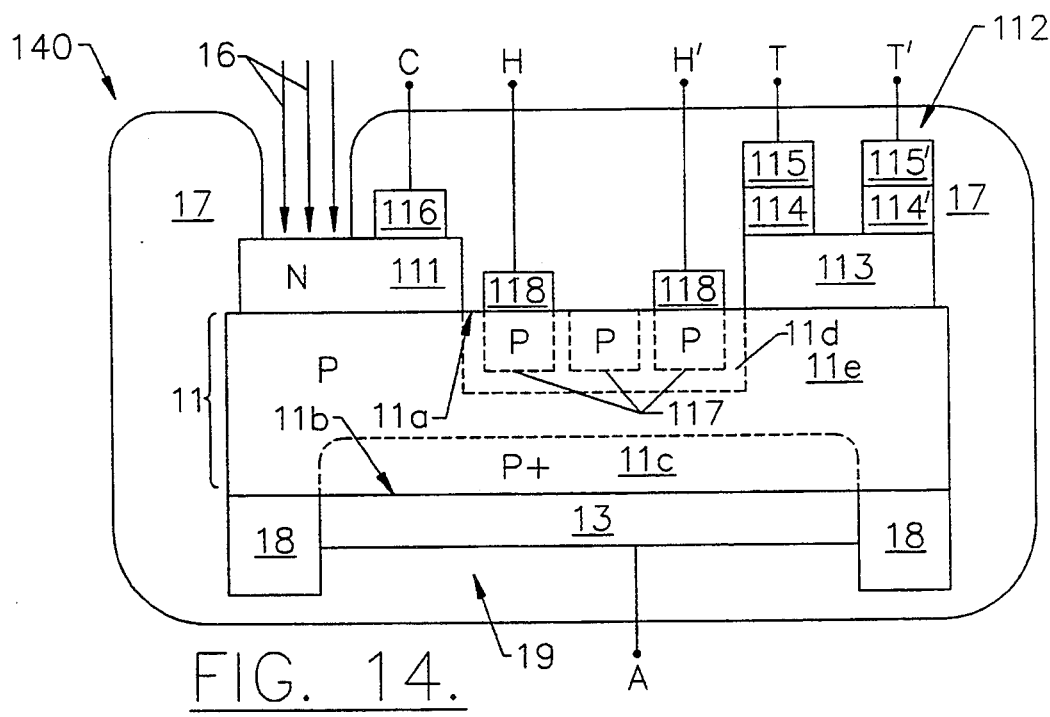
FIG. 14 illustrates a cross-sectional view of a fourth embodiment of a diamond-based diode chemical sensor according to the invention.
Figure 15:
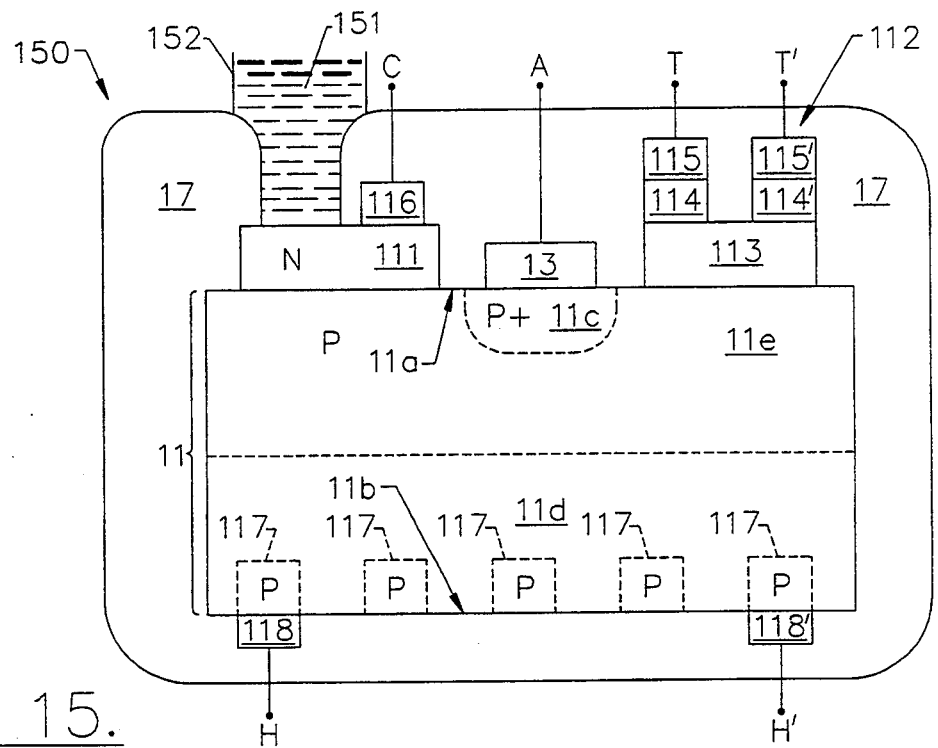
FIG. 15 illustrates a cross-sectional view of a fifth embodiment of a diamond-based diode chemical sensor according to the invention.

FIG. 14 illustrates a fourth embodiment of a diode based sensor 140. As shown, anode contact 13 and P+ layer 11c are formed within an aperture 19 of a substrate 18 as was already described in connection with FIG. 5. FIG. 15 illustrates a fifth embodiment of a diamond-based diode chemical sensor. This sensor 150 is sensitive to chemicals in a liquid 151. The liquid is contained adjacent N-layer 111 by a membrane 152.

Figure 16:
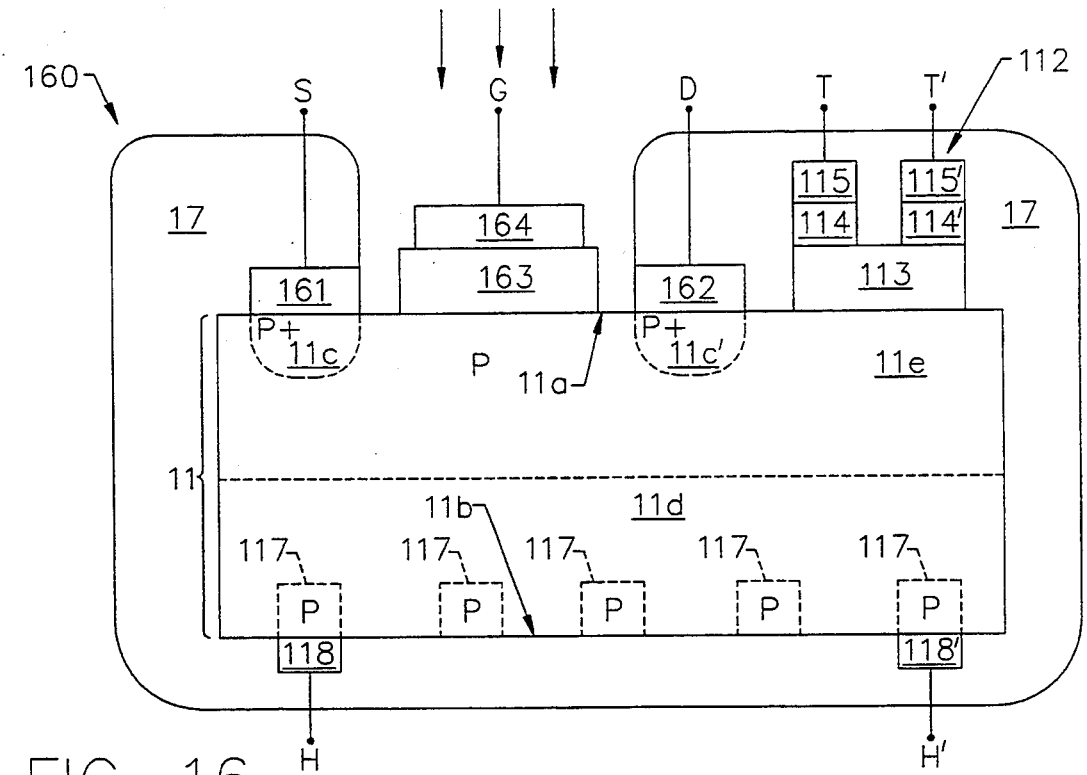
FIG. 16 illustrates a cross-sectional view of a first embodiment of a diamond-based transistor chemical sensor according to the present invention.

Referring now to FIG. 16, a diamond-based transistor chemical sensor is illustrated. As shown, sensor 160 is similar to sensor 110 (FIG. 11) except that a field effect transistor rather than a diode is provided. In order to implement the field effect transistor, a pair of P+ regions 11c, 11c' are provided. A source contact and a drain contact 161, 162 respectively, are provided, and source and drain connections S and D respectively, are also provided. An insulating layer 163 such as silicon dioxide or insulating diamond is provided along with a gate contact 164 which may be a catalytic metal such as palladium. A gate connection G is also provided.

Figure 17:
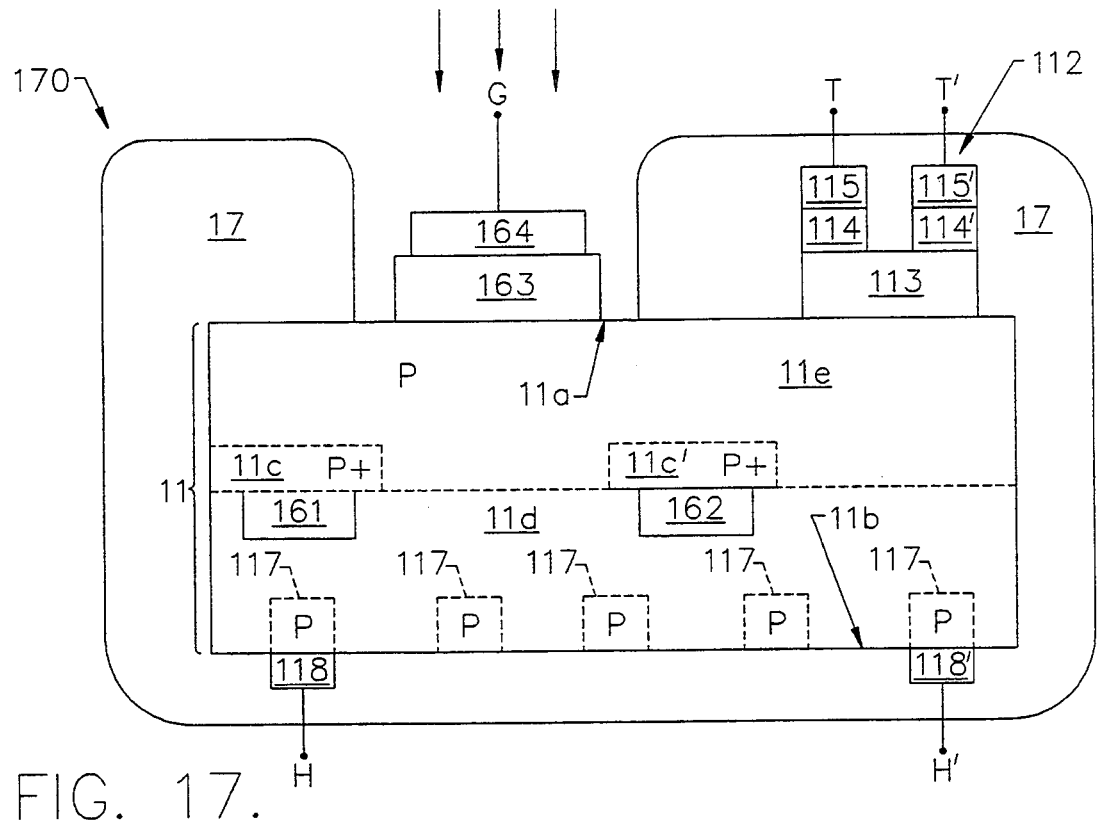
FIG. 17 illustrates a cross-sectional view of a second embodiment of a diamond-based transistor chemical sensor according to the present invention.
Figure 18:
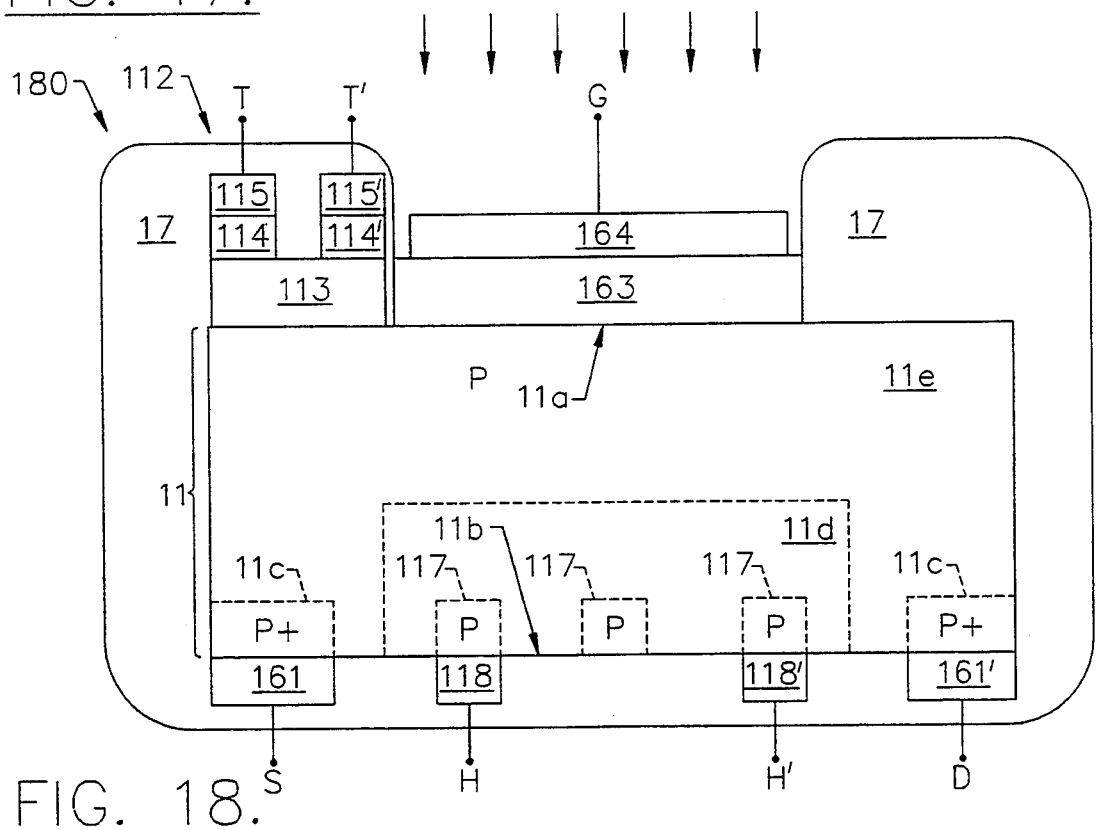
FIG. 18 illustrates a cross-sectional view of a third embodiment of a diamond-based transistor chemical sensor according to the present invention.
Figure 19:
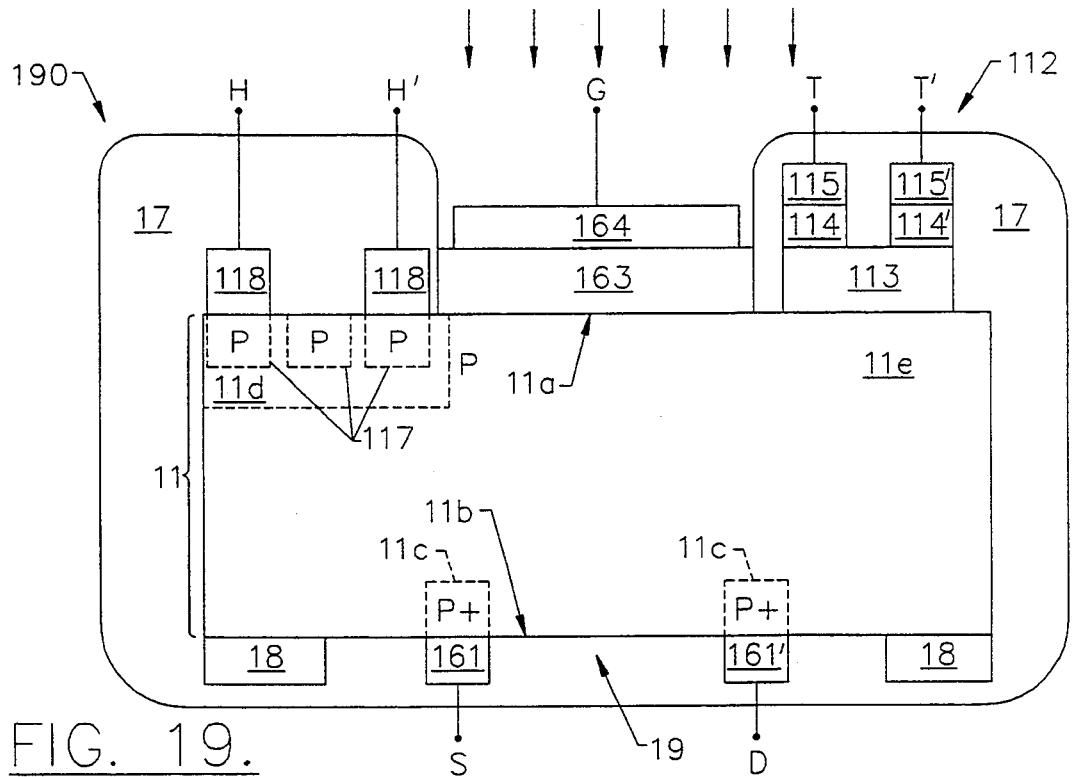
FIG. 19 illustrates a cross-sectional view of a fourth embodiment of a diamond-based transistor chemical sensor according to the present invention.
Figure 20:
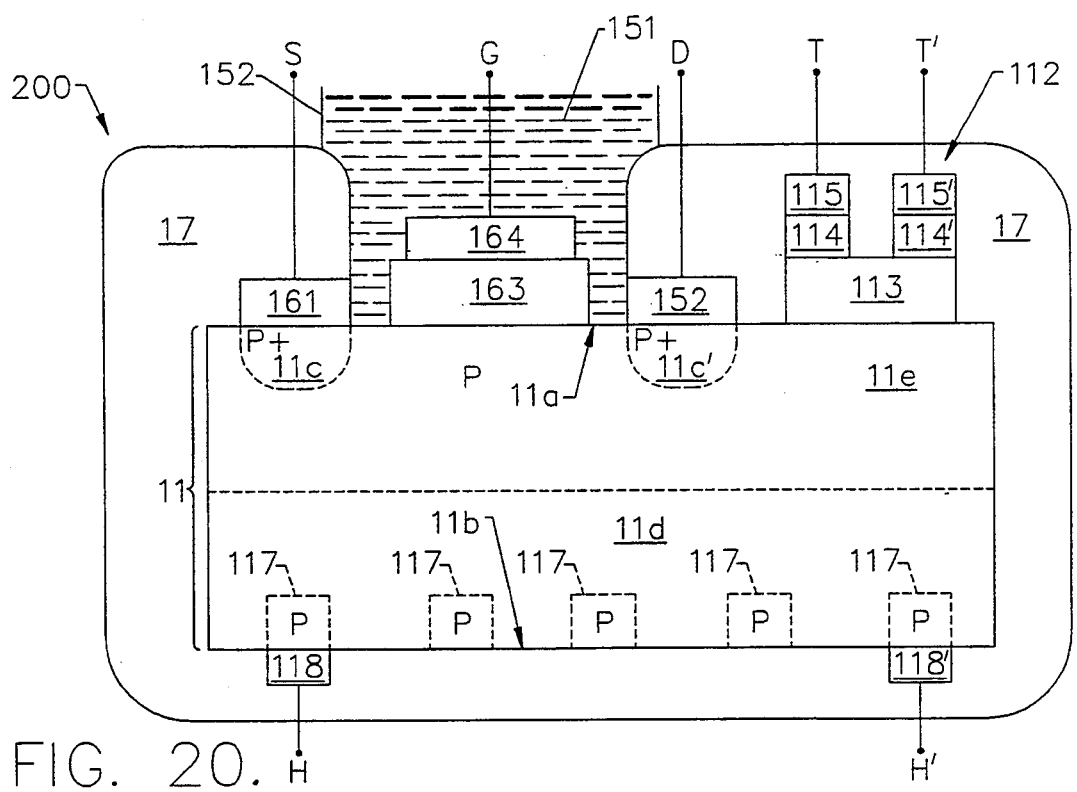
FIG. 20 illustrates a cross-sectional view of a fifth embodiment of a diamond-based transistor chemical sensor according to the present invention.

FIG. 17 illustrates a second embodiment of a diamond-based transistor chemical sensor. Sensor 170 is similar to sensor 150 (FIG. 15), except that source and drain contacts 161 and 162 respectively are buried within diamond layer 11. FIG. 18 illustrates a third embodiment of a diamond-based transistor chemical sensor. Sensor 180 is similar to sensor 170 (FIG. 17), except that source and drain contacts 161, 161' are formed on face 11b of layer 11. FIG. 19 illustrates a fourth embodiment of a diamond-based transistor chemical sensor. Sensor 190 is similar to sensor 180 (FIG. 18), except source and drain contacts 161, 161' are formed in an aperture 19 in substrate 18. FIG. 20 illustrates fifth embodiment of a diamond-based transistor chemical sensor. Sensor 200 is similar to sensor 160 (FIG. 16), except that a membrane 152 is added for detection of ionic species in the liquid 151.

Figure 21:
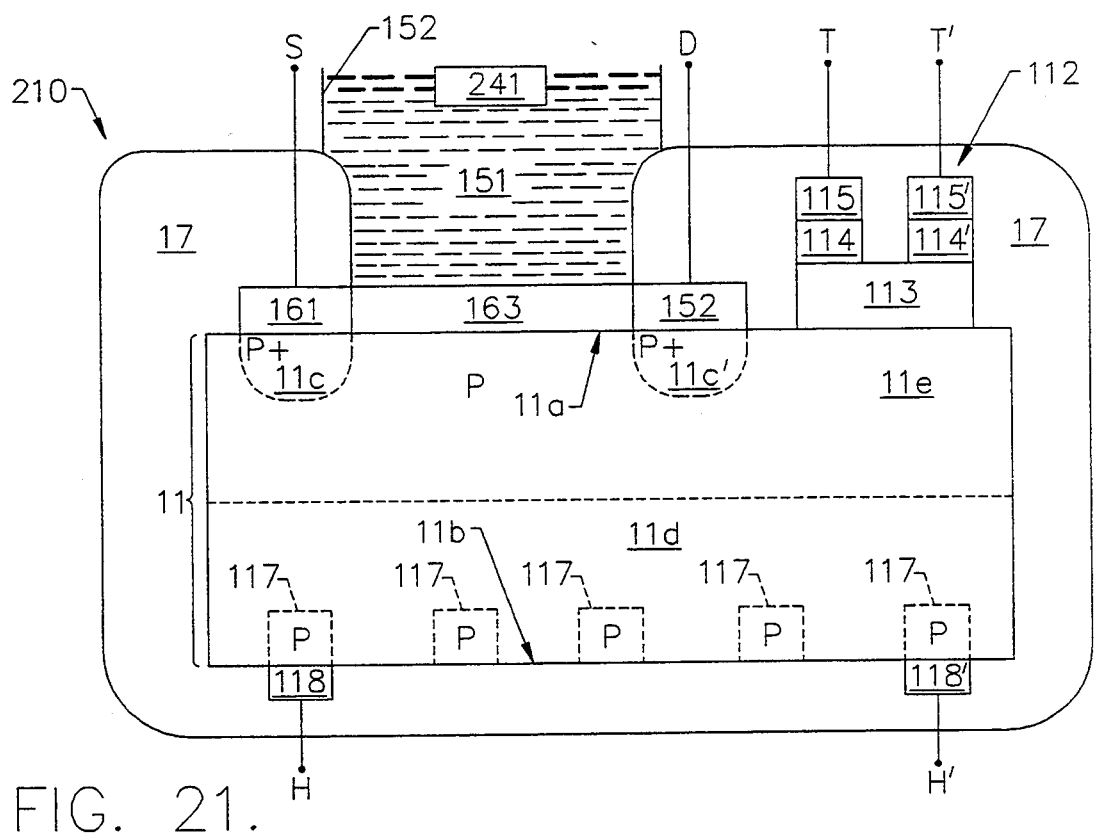
FIG. 21 illustrates a cross-sectional view of a sixth embodiment of a diamond-based transistor chemical sensor according to the present invention.

FIG. 21 illustrates a sixth embodiment of a diamond-based transistor chemical sensor. Sensor 210 is similar to sensor 200 (FIG. 20) except that a reference electrode 241, which is spaced apart from insulating layer 163, is used. This configuration of an insulating layer and a spaced apart reference electrode with an electrolyte solution 151 therebetween is similar to the configuration described in a publication entitled *Hydrogeninated Amorphous Silicon Technology for Chemically Sensitive Thin-Filmed Transistors* by Mariucci et al., Sensors and Actuators, Vol. B6, pp. 29–33 (1992), the disclosure of which is hereby incorporated herein by reference.

Figure 22:
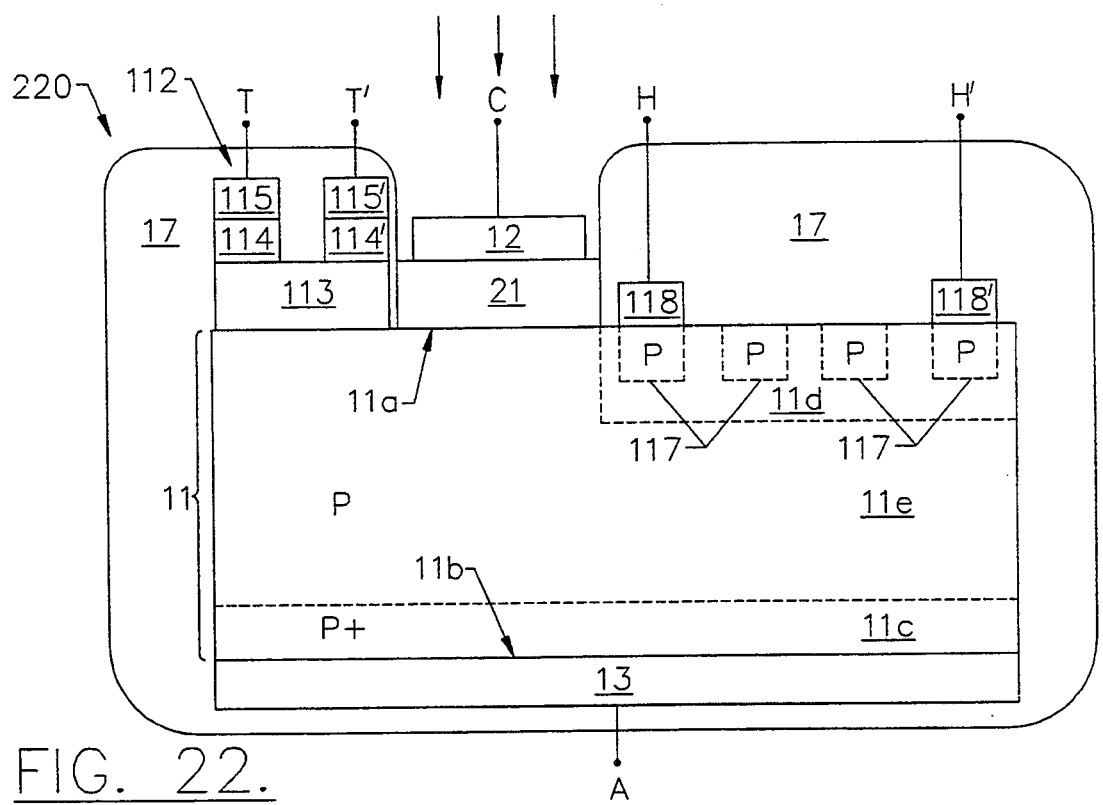
FIG. 22 illustrates a cross-sectional view of an elevated temperature chemical sensor according to the present invention.

FIG. 22 illustrates a Schottky diode chemical sensor according to the present invention. As shown, sensor 220 is similar to sensor 10 of FIG. 1 except a temperature monitor 112 and interdigitated resistive heater 117 have been added. The temperature monitor and resistive heater allow the Schottky diode to operate at an elevated temperature above ambient temperature.

It will be understood by those having skill in the art that a relatively thick insulating layer 21 may be used to form an MOS capacitor rather than a Schottky diode. For example, an insulating layer between 1000–2000 Å thick may be used to form an MOS capacitor. It will be understood by those having skill in the art that the capacitance of the MOS capacitor changes similar to that of the Schottky diode in response to changes in gas concentration. Either the metal gate 12 or the insulator 21 may be formed of a gas sensitive material which affect the capacitance measurements performed on the device. For example, a catalytic metal such as platinum may be used for layer 21 as described for example in Lundström et al., *Physics With Catalytic Metal Gate Chemical Sensors*, CRC Critical Reviews in Solid State and Materials Sciences, Vol. 15, Issue 3, pp. 201–278 (1989), the disclosure of which is hereby incorporated herein by reference.

Operation of the sensors described in FIGS. 11–22 will now be described. By providing a highly doped region 11c, 11c' which provides a low resistance ohmic contact for anode 13, source 161, and drain 162, the frequency dependence of the measured capacitance can be significantly reduced or even eliminated. Thus the frequency dependence of the capacitance/voltage characteristics is reduced significantly. Moreover, by providing diamond-based diode and transistor sensors, high sensitivity may be achieved at high temperatures. The interdigitated resistive heater 117 can be used to maintain the device at elevated temperatures such as between 300°–700° C., for optimal sensitivity, and the temperature monitor 112 can be used to monitor the sensor temperature.

Thus, the inherent advantages of diamond compared to silicon or gallium arsenide as a semiconductor can be exploited in the chemical sensors of the present invention, to provide high temperature, high speed and high power chemical sensors. Moreover, chemical sensors are the most difficult sensors to encapsulate and integrate into state-of-the-art electronics because of the harsh environments in which they operate. Utilization of diamond as a chemical sensing semiconductor may reduce the need to encapsulate the device because of diamond's inherent chemical robustness.

Figure 23:
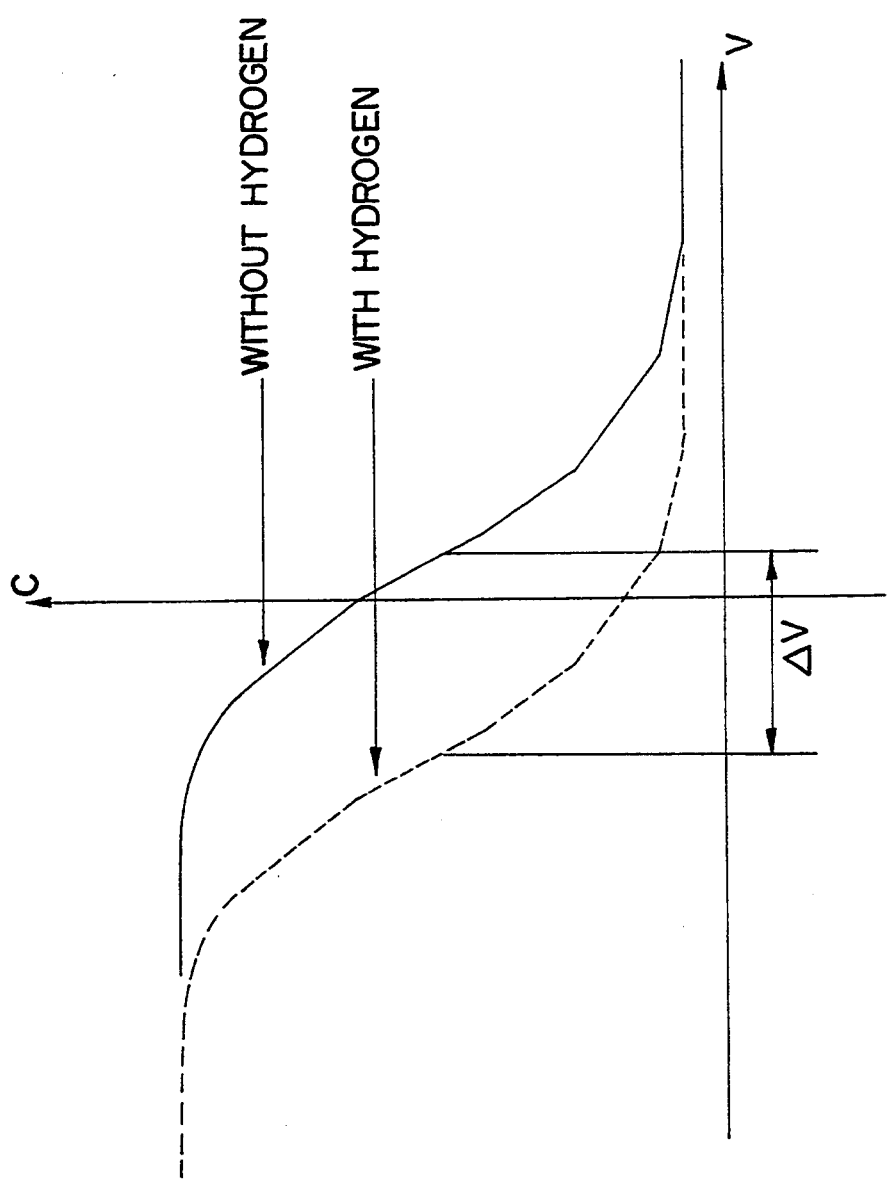
FIG. 23 graphically illustrates representative capacitance versus voltage changes for the diode chemical sensors of FIGS. 11–15.

In fabricating diodes or transistors as shown in FIGS. 11–22, it will be understood that either the insulating layer 163, 21 or the cathode/gate contact 164, 12 or both, can be the sensing material. For example, platinum on silicon dioxide on P-type diamond acts as a hydrogen sensor. While not wishing to be bound by any theory, it is hypothesized that hydrogen molecules or atoms absorb on the metal surface and change the surface potential of the metal, resulting in a shift of a capacitance/voltage (C-V) curve relative to the measurement in the absence of hydrogen. However, any change in the insulator or metal gate due to an adsorbed or absorbed gas will affect the C-V curve. A typical C-V curve is illustrated in FIG. 23. Accordingly, the choice of insulator or metal gate may vary depending upon the chemical to be sensed.

Figure 24:
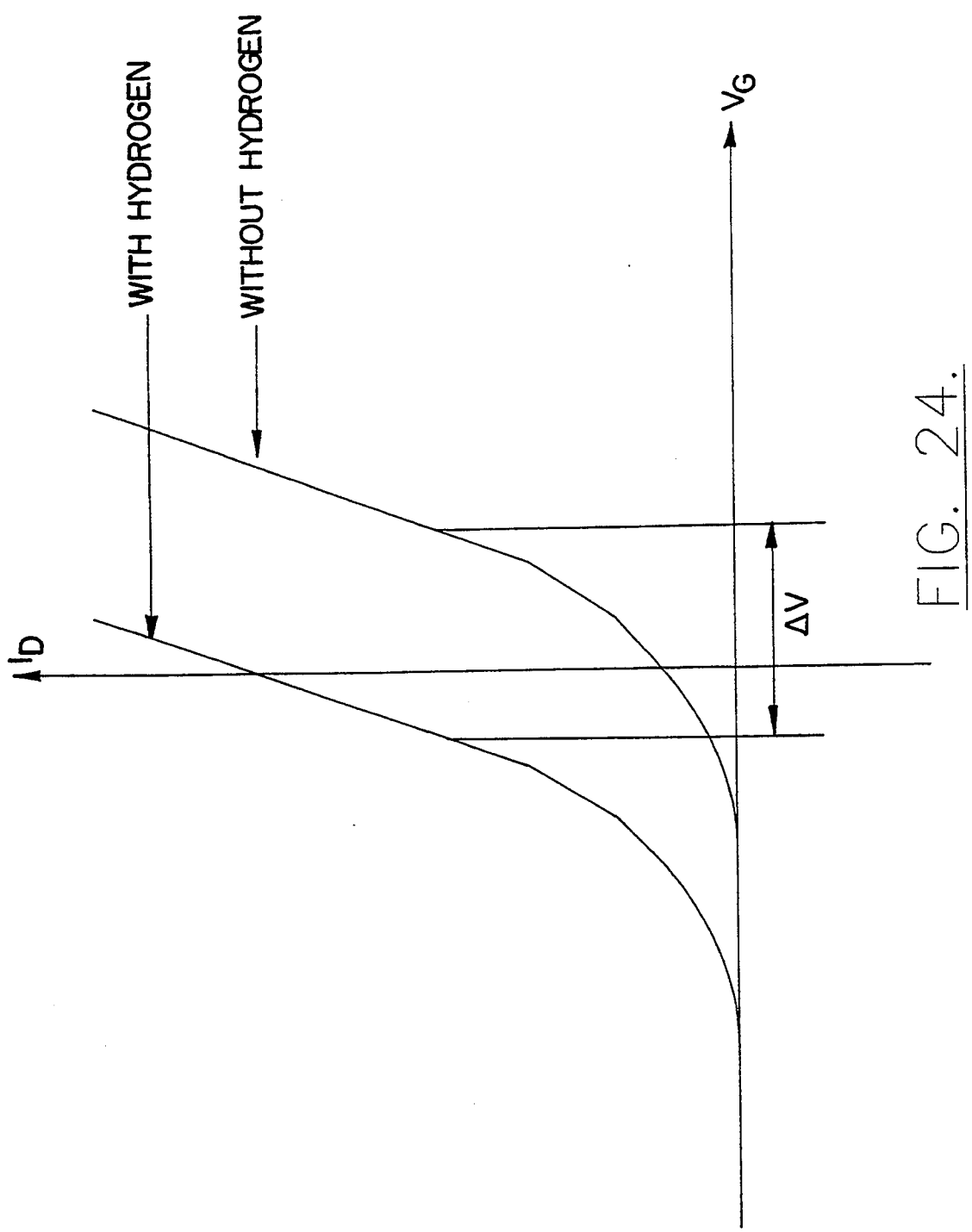
FIG. 24 graphically illustrates changes in transistor characteristics for the transistor based sensors of FIGS. 16–21.

In designing a P-N chemical sensitive diode, many gas sensitive oxides may be used to make a heterojunction with P-type diamond, resulting in a gas sensitive diode. As discussed above for a field effect transistor/capacitor structure, any modification of the gas sensitive material in the device will affect the capacitance-voltage curve. Additionally, the presence of the gas should be apparent in current-voltage (I-V) measurements for a field effect transistor. The expected current or voltage response of a field effect transistor is illustrated in FIG. 24 which is a plot of drain current versus gate voltage for constant source and drain voltage.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A diamond-based chemical sensor comprising:
   a first diamond layer having a first conductivity type;
   a second semiconductor layer of a second conductivity type on said first diamond layer, said first and second layers forming a semiconductor junction therebetween;
   at least one of said first and second layers being configured to allow a chemical external to said diamond-based chemical sensor to interact with said at least one of said first and second layers and alter an electrical characteristic of said semiconductor junction.

2. The diamond-based chemical sensor of claim 1 wherein said first diamond layer is a P-type diamond layer and wherein said second semiconductor layer is selected from the group consisting of an N-type gas sensitive second diamond layer, an N-type moisture sensitive second semiconductor layer, an N-type gas sensitive semiconducting oxide layer and an N-type carbon layer.

3. The diamond-based chemical sensor of claim 1 further comprising:
   an electrical contact on said first diamond layer; and
   a region of said first conductivity type in said first diamond layer, adjacent said electrical contact and which is highly doped relative to said first diamond layer, such that said electrical contact forms an ohmic contact with said region.

4. The diamond-based chemical sensor of claim 3 wherein said electrical contact is on said first diamond layer opposite said second semiconductor layer, said diamond-based chemical sensor further comprising a substrate on said first diamond layer, opposite said second semiconductor layer, and surrounding said electrical contact.

5. The diamond-based chemical sensor of claim 4 further comprising heating means in said substrate, for heating said diamond sensor above an ambient temperature.

6. The diamond-based chemical sensor of claim 5 wherein said substrate is an undoped diamond substrate.

7. The diamond-based chemical sensor of claim 1 further comprising means, thermally coupled to at least one of said first and second layers, for heating said diamond sensor above an ambient temperature.

8. The diamond-based chemical sensor of claim 7 further comprising an undoped diamond layer on said first diamond layer, opposite said second semiconductor layer, and wherein said heating means comprises a resistive heater in said undoped diamond layer.

9. The diamond-based chemical sensor of claim 7 further comprising means, thermally coupled to at least one of said first and second layers, for monitoring the temperature of said diamond-based chemical sensor.

10. The diamond-based chemical sensor of claim 1 further comprising means for confining a chemical containing liquid adjacent one of said first and second layers.

11. The diamond-based chemical sensor of claim 1 further comprising:
   a substrate on said first diamond layer opposite said second semiconductor layer, said substrate having an aperture therein for exposing said first diamond layer;
   an electrical contact on said first diamond layer in said aperture; and
   a region of said first conductivity type in said first diamond layer, adjacent said electrical contact and which is highly doped relative to said first diamond layer, such that said electrical contact forms an ohmic contact with said region.

12. A diamond-based chemical sensor comprising:
   a diamond layer;
   a transistor in said diamond layer, said transistor including a controlling electrode, a first controlled electrode and a second controlled electrode;
   said controlling electrode being configured to allow a chemical external to said diamond-based chemical sensor to interact with said controlling electrode and alter an electrical characteristic of said transistor.

13. The diamond-based chemical sensor of claim 12 wherein said transistor is a field effect transistor, wherein said controlling electrode is a gate electrode, wherein said first controlled electrode is a source electrode and wherein said second controlling electrode is a drain electrode.

14. The diamond-based chemical sensor of claim 13 wherein said gate electrode comprises an insulating layer on said diamond layer and a gate contact on said gate insulating layer, opposite said diamond layer, at least one of said insulating layer and said gate contact being selected to allow a chemical external to said diamond-based chemical sensor to interact therewith, and alter the characteristics of said field effect transistor.

15. The diamond-based chemical sensor of claim 12 wherein said first controlled electrode includes a first electrical contact on said diamond layer and a first region adjacent said first electrical contact and which is highly doped relative to said diamond layer, such that said first electrical contact forms a first ohmic contact with said first region; and wherein said second controlled electrode includes a second electrical contact on said diamond layer and a second region adjacent said second electrical contact and which is highly doped relative to said diamond layer, such that said second electrical contact forms a second ohmic contact with said second region.

16. The diamond-based chemical sensor of claim 13 wherein said source, drain and gate electrodes are formed on a first face of said diamond layer.

17. The diamond-based chemical sensor of claim 13 wherein said gate electrode is formed on a first face of said diamond layer and wherein said source electrode and said drain electrode are formed on a second face of said diamond layer.

18. The diamond-based chemical sensor of claim 16 further comprising a substrate on said diamond layer, opposite said source, drain and gate electrodes.

19. The diamond-based chemical sensor of claim 18 further comprising heating means in said substrate, for heating said diamond sensor above an ambient temperature.

20. The diamond-based chemical sensor of claim 19 wherein said substrate is an undoped diamond substrate.

21. The diamond-based chemical sensor of claim 17 further comprising a substrate on said second face, and surrounding said source and drain electrodes.

22. The diamond-based chemical sensor of claim 21 further comprising heating means in said substrate, for heating said diamond sensor above an ambient temperature.

23. The diamond-based chemical sensor of claim 22 wherein said substrate is an undoped diamond substrate.

24. The diamond-based chemical sensor of claim 12 further comprising means, thermally coupled to at least one of said diamond layer, for heating said diamond-based sensor above an ambient temperature.

25. The diamond-based chemical sensor of claim 24 further comprising an undoped second diamond layer on said first diamond layer, opposite said gate electrode, and wherein said heating means comprises a resistive heater in said undoped second diamond layer.

26. The diamond-based chemical sensor of claim 24 further comprising means, thermally coupled to at least one of said first and second layers, for monitoring the temperature of said diamond-based chemical sensor.

27. The diamond-based chemical sensor of claim 12 further comprising means for confining a chemical containing liquid adjacent said gate electrode.

28. The diamond-based chemical sensor of claim 27 wherein said gate electrode is spaced apart from said insulating layer, and wherein said confining means confines said chemical containing liquid between said gate electrode and said insulating layer.

29. A diamond-based chemical sensor comprising:
a diamond layer;
a chemically sensitive layer on said diamond layer;
heating means, thermally coupled to said diamond layer, for heating said diamond-based chemical sensor above an ambient temperature; and
temperature monitoring means, thermally coupled to said diamond layer, for monitoring the temperature of said diamond-based chemical sensor.

30. The diamond-based chemical sensor of claim 29 wherein said heating means is a resistive heating means in said diamond layer.

31. The diamond-based chemical sensor of claim 29 wherein said temperature monitoring means includes at least a second diamond layer on said diamond layer.

32. The diamond-based chemical sensor of claim 30 wherein said temperature monitoring means includes at least a second diamond layer on said diamond layer.

33. The diamond-based chemical sensor of claim 29 further comprising at least one electrode, said at least one electrode in combination with at least said diamond layer and said chemically sensitive layer forming one of a junction diode, a Schottky diode, a capacitor and a transistor.

* * * * *